US011925468B2

(12) United States Patent
Rottmann et al.

(10) Patent No.: US 11,925,468 B2
(45) Date of Patent: Mar. 12, 2024

(54) METHOD AND SYSTEM FOR THE IDENTIFICATION AND MODELING OF ATRIAL FIBRILLATION REENTRY

(71) Applicant: Northwestern University, Evanston, IL (US)

(72) Inventors: Markus Rottmann, Chicago, IL (US); Rishi K. Arora, Chicago, IL (US)

(73) Assignee: Northwestern University, Evanston, IL (US)

( * ) Notice: Subject to any disclaimer, the term of this patent is extended or adjusted under 35 U.S.C. 154(b) by 170 days.

(21) Appl. No.: 17/521,545

(22) Filed: Nov. 8, 2021

(65) Prior Publication Data

US 2022/0142551 A1 May 12, 2022

Related U.S. Application Data

(60) Provisional application No. 63/111,282, filed on Nov. 9, 2020.

(51) Int. Cl.
  *A61B 5/361* (2021.01)
  *A61B 5/367* (2021.01)
(52) U.S. Cl.
  CPC .............. *A61B 5/361* (2021.01); *A61B 5/367* (2021.01)
(58) Field of Classification Search
  CPC .................................. A61B 5/361; A61B 5/367
  See application file for complete search history.

(56) References Cited

U.S. PATENT DOCUMENTS

| | | | |
|---|---|---|---|
| 2005/0209524 A1* | 9/2005 | Donaldson | A61N 1/3625 600/510 |
| 2010/0094274 A1* | 4/2010 | Narayan | A61B 7/04 600/509 |
| 2013/0004049 A1* | 1/2013 | Weeden | G06T 7/73 382/131 |
| 2014/0276152 A1* | 9/2014 | Narayan | A61B 5/316 600/508 |
| 2015/0216435 A1 | 8/2015 | Bokan et al. | |
| 2017/0172440 A1 | 6/2017 | Arora | |
| 2018/0055813 A1 | 3/2018 | Kurz et al. | |
| 2018/0103865 A1* | 4/2018 | Trayanova | A61B 5/0059 |
| 2018/0296111 A1* | 10/2018 | Deno | A61B 5/746 |

(Continued)

OTHER PUBLICATIONS

Lewis T, Drury AN and Iliescu CC. Further observations upon the state of rapid re-excitation of the auricles. Heart-J Stud Circ. 1921; 8:311-339.

(Continued)

*Primary Examiner* — Catherine M Voorhees
*Assistant Examiner* — Roland Dinga
(74) *Attorney, Agent, or Firm* — Bell & Manning, LLC

(57) ABSTRACT

A method for characterizing atrial fibrillation includes determining, by a processor of a computing device and based on heart data, an earliest activation time of a heart being monitored. The method also includes determining, by the processor and based on the heart data, a latest activation time of the heart. The method also includes modeling, by the processor, the earliest activation time and the latest activation time within one or more activation time maps. The method further includes identifying, by the processor, an atrial fibrillation driver based at least in part on the one or more activation time maps.

18 Claims, 24 Drawing Sheets

(56) References Cited

U.S. PATENT DOCUMENTS

2019/0275339 A1* 9/2019 Ghosh .................. A61N 1/3684
2020/0196891 A1* 6/2020 Timofeyev ............. A61B 5/367

OTHER PUBLICATIONS

Allessie MA, Lammers WJ, Bonke IM and Hollen J. Intra-atrial reentry as a mechanism for atrial flutter induced by acetylcholine and rapid pacing in the dog. Circulation. 1984; 70:123-35.

Haissaguerre M, Jais P, Shah DC, Takahashi A, Hocini M, Quiniou G, Garrigue S, Le Mouroux A, Le Metayer P and Clementy J. Spontaneous initiation of atrial fibrillation by ectopic beats originating in the pulmonary veins. N Engl J Med. 1998; 339:659-66.

Sahadevan J, Ryu K, Peltz L, Khrestian CM, Stewart RW, Markowitz AH and Waldo AL. Epicardial mapping of chronic atrial fibrillation in patients—Preliminary observations. Circulation. 2004; 110:3293-3299.

Sanders P, Berenfeld O, Hocini MZ, Jais P, Vaidyanathan R, Hsu LF, Garrigue S, Takahashi Y, Rotter M, Sacher F, Scavee C, Ploutz-Snyder R, Jalife J and Haissaguerre M. Spectral analysis identifies sites of high-frequency activity maintaining atrial fibrillation in humans. Circulation. 2005; 112:789-797.

Cuculich PS, Wang Y, Lindsay BD, Faddis MN, Schuessler RB, Damiano RJ, Li L and Rudy Y. Noninvasive Characterization of Epicardial Activation in Humans with Diverse Atrial Fibrillation Patterns. Circulation. 2010; 122:1364.

Swarup V, Baykaner T, Rostamian A, Daubert JP, Hummel J, Krummen DE, Trikha R, Miller JM, Tomassoni GF and Narayan SM. Stability of Rotors and Focal Sources for Human Atrial Fibrillation: Focal Impulse and Rotor Mapping (FIRM) of AF Sources and Fibrillatory Conduction. J Cardiovasc Electr. 2014; 25:1284-1292.

The Non-Final Office Action dated Jul. 5, 2023 for U.S. Appl. No. 17/308,756; pp. 1-20.

* cited by examiner

| | |
|---|---|
| Age (y) | 66.0±7.3 |
| Sex, male (%) | 60 |
| BMI | 32.5±7.6 |
| Diabetes mellitus (%) | 10 |
| Hypertension (%) | 60 |
| Type of AF (%) | |
| Paroxysmal AF | 10 |
| Early persistent AF | 90 |
| Long-standing persistent AF | 0 |
| Permanent AF | 0 |
| Duration of AF (months) | 1.6±2.2 |
| Time since first AF episode (years) | 11.0±11.9 |
| Prior ablation procedure (%) | 80 |
| Antiarrhythmic drugs/rate-controlling agents (%) | |
| β-blockers | 70 |
| Calcium channel blockers | 40 |
| Digoxin | 20 |
| Flecainide | 25 |
| Dofetilide | 10 |
| Dronedarone | 20 |
| Amiodarone | 40 |
| Underlying cardiac disease, n (%) | |
| Coronary artery disease | 10 |
| Valvular disease | 70 |
| — Mitral regurgitation | 50 |
| — Mitral stenosis | 10 |
| — Tricuspid regurgitation | 30 |
| Echocardiogram | |
| Biatrial dilatation (%) | 50 |
| LA volume (mL/m$^2$) | 52.6±31.9 |
| Impaired LV function (%) | 50 |
| — LVEF 45%–55% | 10 |
| — LVEF 35%–45% | 30 |
| — LVEF <35% | 10 |

Fig. 2

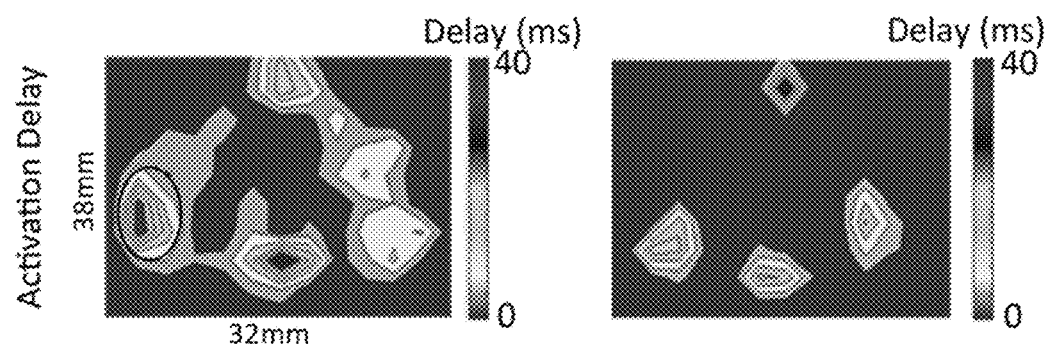
Fig. 4C
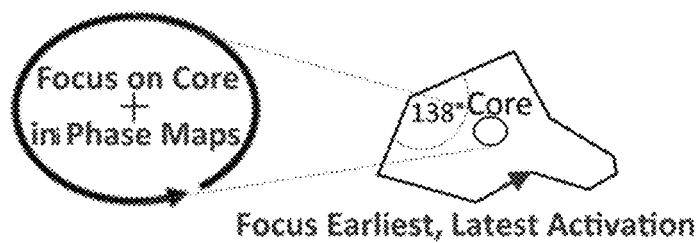
Fig. 4D
Fig. 4E
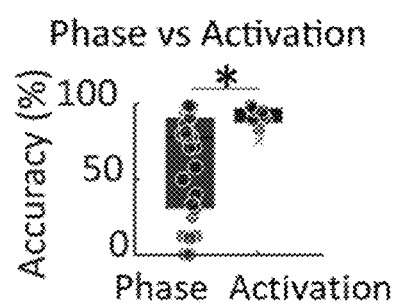
Fig. 4F

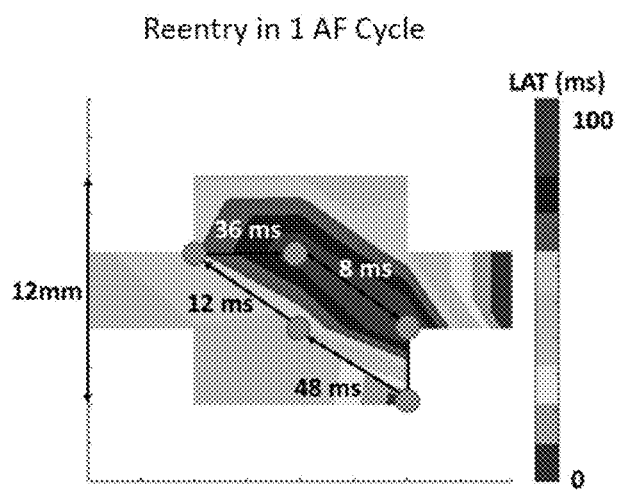 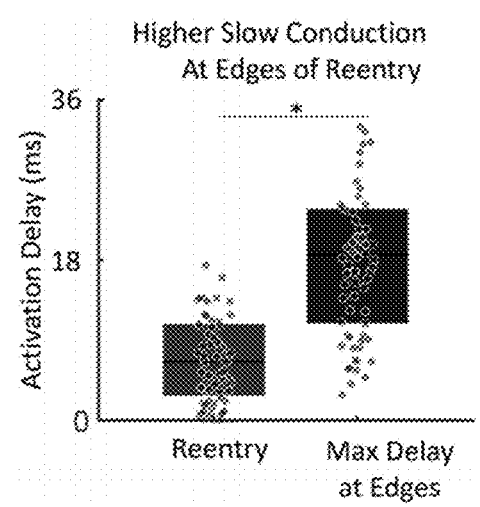
Fig. 8A                                Fig. 8B

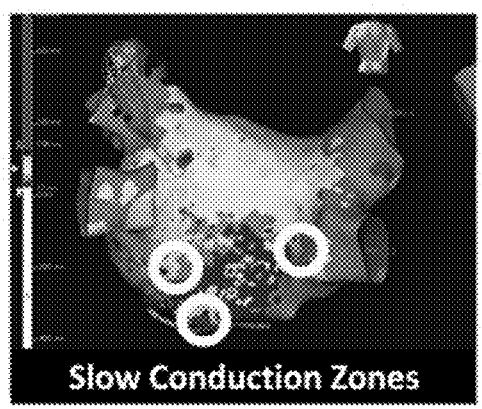 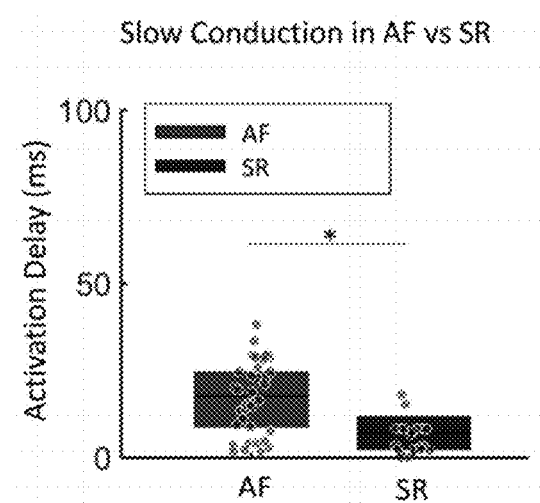
Fig. 8C
Fig. 8D

| | Anatomic Reentry | Functional Reentry | | Structural and Functional Reentry |
|---|---|---|---|---|
| | Circus Movement (Lewis et al. 1921) | Leading Circle (Allessie et al. 1973) | Spiral Wave (Weiner et al. 1946, Jalife et al. 1999) | Polygon Reentry (Rottmann et al. 2020) |
| | WL = CV × RP | | Wavelength | Fiber Crossing / Fibrosis |
| Determinant of circuit size | Anatomical obstacle | CV × RP | Source-sink relationship | Propagation along fibers. Anchoring between slow conduction zones (fiber crossings, fibrofatty zones) |
| Fixed circuit? | Yes | No | No | Frequently anchoring at same locations |
| Resetting and entrainment? | Yes | No | ? | Yes |
| Excitable gap? | Yes | No | Yes | Yes |
| Core | Anatomic obstacle, Unexcitable | Refractory tissue, Unexcitable | Excitable but unexcited | Not main reason for anchoring, Slow conduction edges anchor reentry |
| Revolution time | 1/CV | RP | Determined by excitability properties | Determined by structural and functional properties |

Fig. 9A

Small Slow Conduction Zones

| | |
|---|---|
| Substrate | Are Fiber crossings in all bi-atrial regions |
| | Develop to zones of focal fibrosis and fat |
| Activation delay in activation time maps | Are frequency dependent zones of activation delay |
| | Are anchor zones of rotational activities |
| Dependency of activation patterns, cycle length and rhythm | Increase during rotational activity in AF |
| | Reduce during planar wave activation in AF |
| | Are at the same locations during AF and sinus rhythm |
| Treatment with PVI | Reduce after PVI in all regions remote to the PVs |
| Evaluation | Are detected in human like large animals and patients |

Fig. 9B

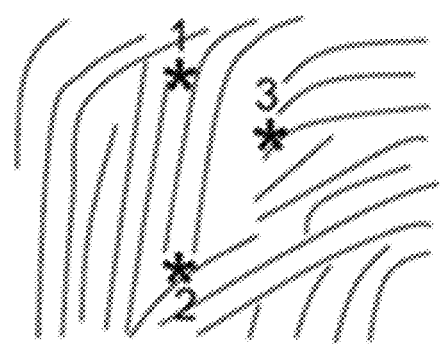
Fig. 9C
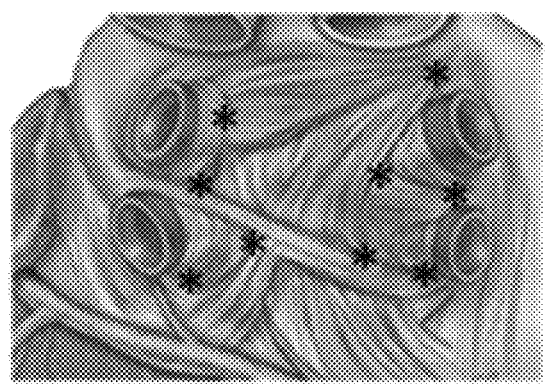
Fig. 9D
Fig. 9E
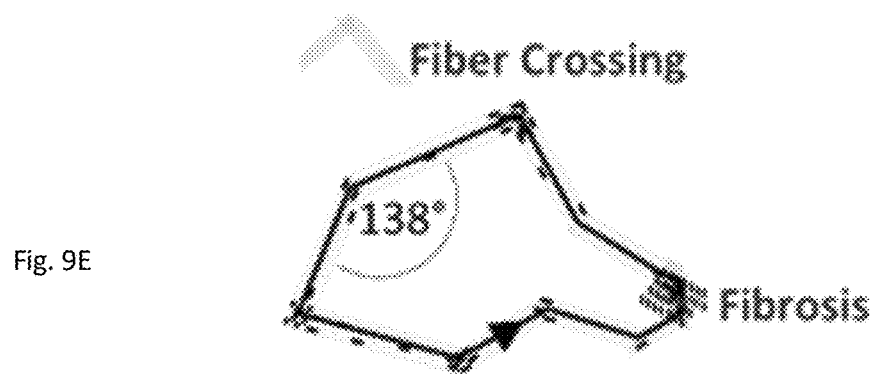

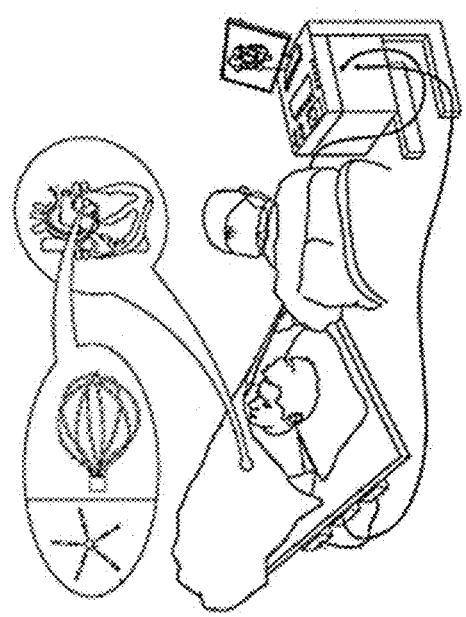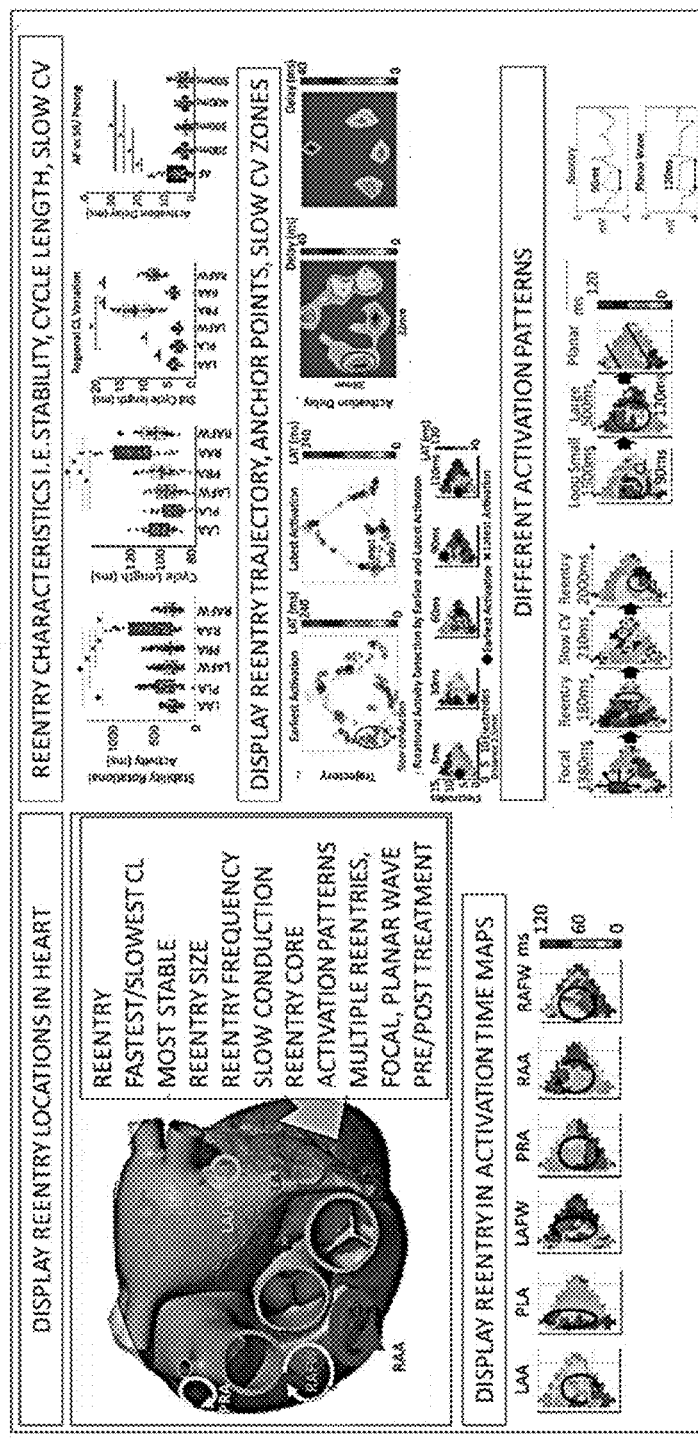
Fig. 10

METHOD AND SYSTEM FOR THE IDENTIFICATION AND MODELING OF ATRIAL FIBRILLATION REENTRY

CROSS-REFERENCE TO RELATED APPLICATIONS

The present application claims the priority benefit of U.S. Provisional App. No. 63/111,282 filed on Nov. 9, 2020, the entire disclosure of which are incorporated by reference herein.

REFERENCE TO GOVERNMENT RIGHTS

This invention was made with government support under HL125881 and HL140061 awarded by the National Institutes of Health (NIH). The government has certain rights in the invention.

BACKGROUND

Atrial fibrillation (AF) refers to a quivering or irregular heartbeat that can cause immediate symptoms such as heart palpitations, chest pain, fatigue, shortness of breath, dizziness, and overall weakness. Atrial fibrillation can also result in various long term health issues such as blood clots, heart failure, stroke, etc. During atrial fibrillation, the atrial (upper) chambers of the heart beat irregularly, which prevents normal blood flow through the (lower) ventricles. A multiple wavelet reentry hypothesis as a mechanism for atrial fibrillation (AF) was proposed in 1959. In 1985, this hypothesis was experimentally confirmed hypothesis by showing that multiple wave fronts throughout the atrium maintain themselves by reentry around continuously shifting areas of functional conduction block. However, despite extensive research, the mechanisms of AF and its treatment are still not entirely clear.

SUMMARY

An illustrative method for characterizing atrial fibrillation includes determining, by a processor of a computing device and based on heart data, an earliest activation time of a heart being monitored. The method also includes determining, by the processor and based on the heart data, a latest activation time of the heart. The method also includes modeling, by the processor, the earliest activation time and the latest activation time within one or more activation time maps. The method further includes identifying, by the processor, an atrial fibrillation driver based at least in part on the one or more activation time maps.

An illustrative system to characterize atrial fibrillation includes a memory configured to store heart data and a processor operatively coupled to the memory. The processor is configured to determine, based on heart data, an earliest activation time of a heart associated with the heart data. The processor is also configured to determine, based on the heart data, a latest activation time of the heart. The processor is also configured to model the earliest activation time and the latest activation time within one or more activation time maps. The processor is further configured to identify an atrial fibrillation driver based at least in part on the one or more activation time maps.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

FIG. 2 is a table that summarizes overall patient and animal characteristics in accordance with an illustrative embodiment.

FIG. 4C depicts slow conduction zones at the edges of the earlies trajectory in accordance with an illustrative embodiment.

FIG. 4D shows reentrant circuit trajectory of the historically circular reentry model in accordance with an illustrative embodiment.

FIG. 4E shows the redefined reentrant circuit trajectory in the form of a polygon in accordance with an illustrative embodiment.

FIG. 4F depicts the accuracy of detected rotational activity in the RAA based on previously described established phase singularity method (left) and on the completely new algorithm based on earliest and latest activation (right) in accordance with an illustrative embodiment.

FIG. 8A shows an activation time map of one AF cycle in the PLA that exhibits a reentrant circuit with a 2-6-fold higher activation delay at one edge of the reentrant trajectory compared to the other reentry trajectory segment parts in accordance with an illustrative embodiment.

FIG. 8B shows that activation delay and maximal activation delay at reentries per AF cycle were 9.3±8.8 ms (median 9.2 ms) and 20.2±8.1 ms (median 19.6 ms) along 2.5 in accordance with an illustrative embodiment.

FIG. 8C shows three major zones of slow conduction on a representative left atrial bipolar voltage map and the corresponding activation time map in the Ensite NavX mapping system® (Abbott) in accordance with an illustrative embodiment.

FIG. 8D shows how the activation delay was 2× higher in AF compared to SR/CS-pacing maps in accordance with an illustrative embodiment.

FIG. 9A is a table comparing circus movement, leading circle, spiral wave, and the proposed polygon reentry models in accordance with an illustrative embodiment.

FIG. 9B summarizes the main findings of the present study in accordance with an illustrative embodiment.

FIG. 9C depicts an example of the PLA in accordance with an illustrative embodiment.

FIG. 9D depicts fiber orientation in the PLA with multiple fiber crossings near the pulmonary veins in accordance with an illustrative embodiment.

FIG. 9E is a schematic of the proposed polygon reentry model in accordance with an illustrative embodiment.

FIG. 10 is a diagram that shows use of the proposed techniques by a physician to identify and display reentry in accordance with an illustrative embodiment.

DETAILED DESCRIPTION

Figure 1:
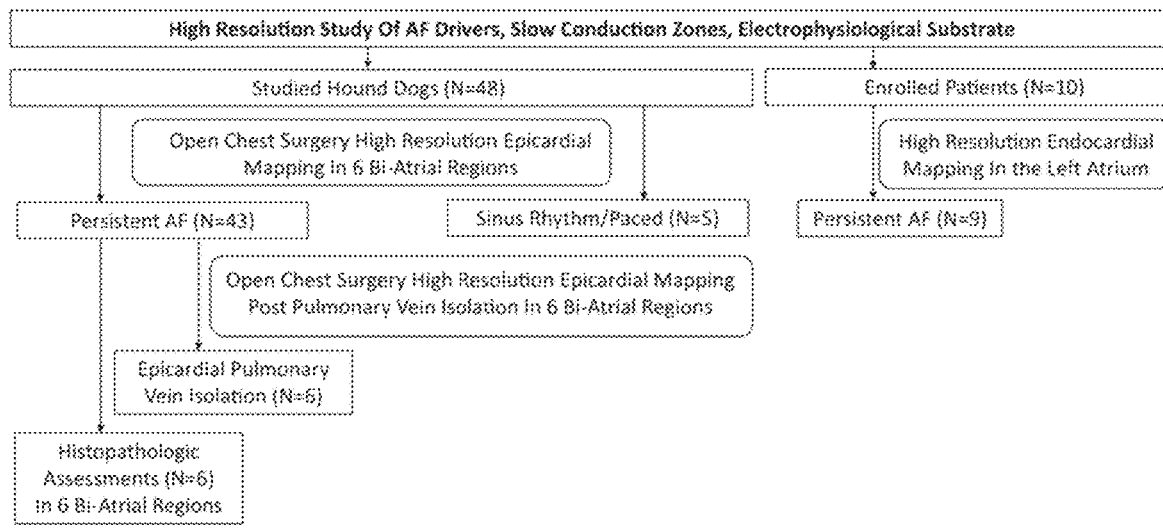
FIG. 1 is a diagram illustrating parameters of the study in accordance with an illustrative embodiment.
Figure 3A:
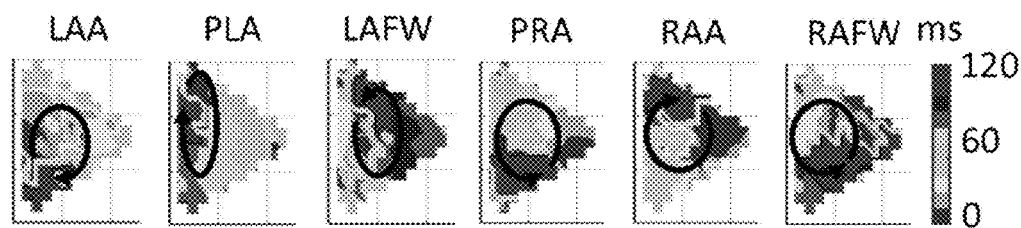
FIG. 3A shows a representative example (heart #10) of detected rotations activities in accordance with an illustrative embodiment.
Figure 3B:
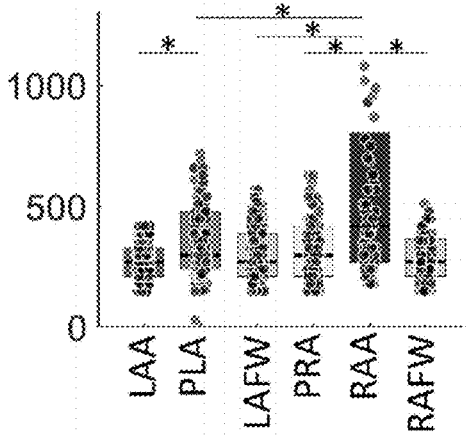
FIG. 3B illustrates how the highest stability of rotational activities was detected in the RAA and second in the PLA in accordance with an illustrative embodiment.
Figure 3C:
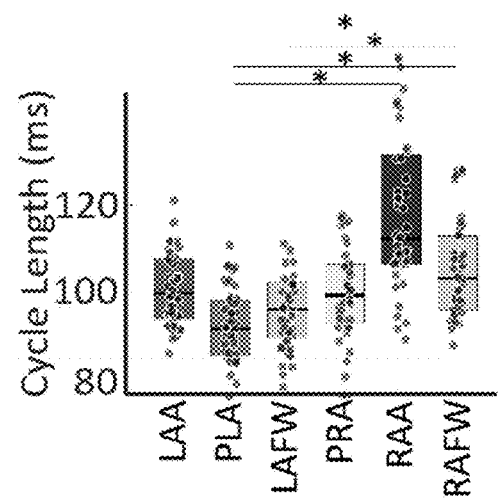
FIG. 3C shows regional distribution of CL in accordance with an illustrative embodiment.
Figure 3D:
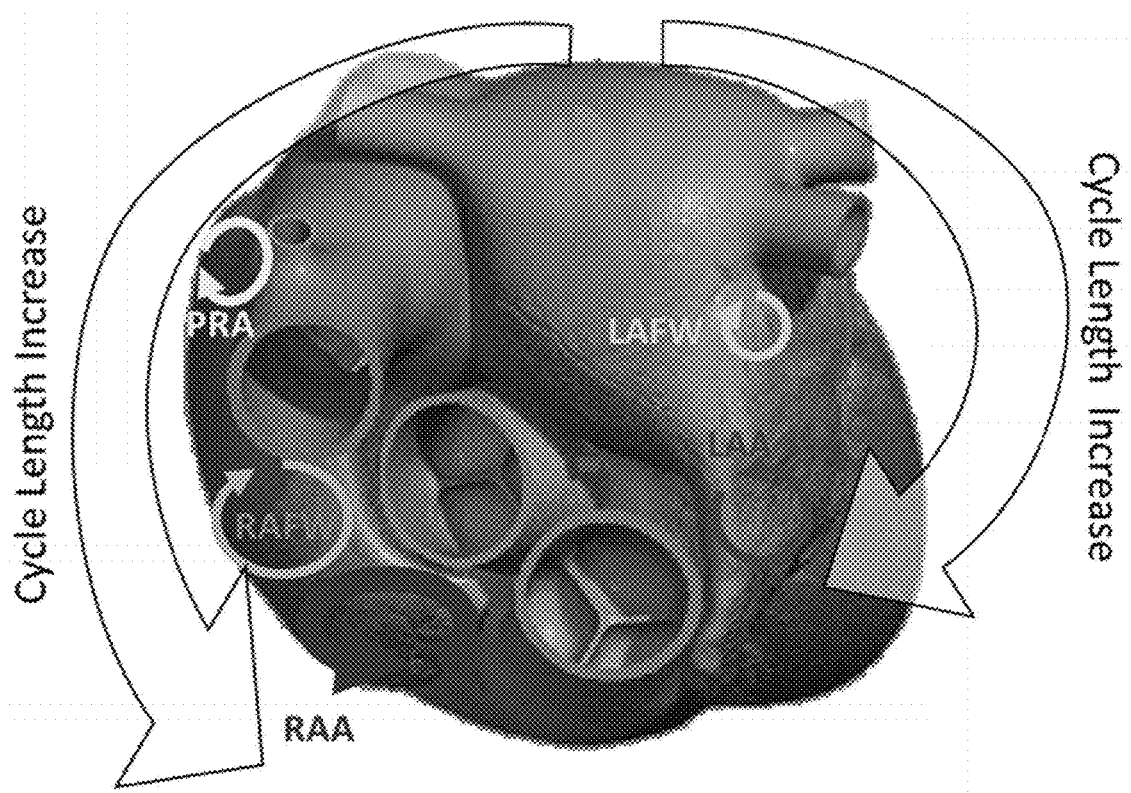
FIG. 3D depicts cycle length increase with increasing distance to the pulmonary veins in the six bi-atrial regions in accordance with an illustrative embodiment.

Described herein are methods and systems to detect and treat atrial fibrillation (AF). As discussed in more detail below, the inventors have performed high-density mapping of persistent atrial fibrillation (AF) in animals and patients (1) to test that AF is due to ≥1 reentries, and (2) to characterize activation delay and reentries pre/post pulmonary vein isolation (PVI). Based on this research, electrophysiological characteristics were identified that can predispose to the induction, maintenance, and reduction of AF. Additionally, a new polygon reentry model for AF was developed. The polygon reentry model describes for the first time both structural and functional mechanisms based on a novel reentry detection algorithm tracking the earliest and latest activation. The polygon reentry model is a completely new reentry model, and only 4 reentry models have been developed in the last 100 years. The proposed model provides a new and better understanding of atrial fibrillation (AF) mechanisms and explains for the first time both functional and structural mechanisms in AF. Additionally, the new algorithm to detect these polygon reentry models is based on a new detection method, which for the first time detects the earliest activation. This a completely new method and way to uncover AF drivers responsible for atrial fibrillation.

As discussed in more detail below, in one study, the inventors performed high-density mapping of persistent AF in both 48 open-chest dogs (3-14 weeks rapid atrial pacing, 117 electrodes, 2.5 mm distance, in both atria) and 10 patients. In contrast to historical circular reentry models, the new algorithm revealed that the reentry shape followed unique line patterns in form of a 'polygon' with slow conduction (defined as >10 ms per 2.5 mm) at the edges of these line patterns. The trajectory at edges had four-fold slower conduction (activation delay 15±5 ms) vs. the rest of trajectory providing anchoring of stable reentry (stability 120-4940 ms). This new algorithm was 26% more accurate in reentry detection than the established phase singularity method. Slow conduction zones corresponded to myocyte bundle nodal points/fibro-fatty zones. The degree of dense fibro-fatty zones correlated with slow conduction zones (R=0.7, P<0.05), and myocyte bundle nodal point density correlated with the stability of rotational activity (R=0.6, P<0.05). Slow conduction zones had two-fold higher activation delay in AF vs. sinus rhythm (SR). Pulmonary vein isolation (PVI) in five animals reduced slow conduction zones and stability of rotational drivers in the posterior left atrium (PLA) and regions remote from the PVs. In persistent AF patients, HD-grid-catheter-mapping (16 electrodes, 3 mm dist.) revealed 2× higher activation delay at trajectory edges vs. the rest (maximal delay 20.5±8.1 ms vs 9.3±8.8 ms) (P<0.01) and 1.4× higher during AF 18.0±11.6 ms vs. SR/CS-pacing 13.0±18.7 ms (P<0.01).

Based on this data, it was determined that reentry propagation follows unique line patterns in form of a polygon with slow conduction at the edges of these line patterns. The proposed new reentry detection method was found to be more accurate than established phase methods. It was also determined that reentries frequently anchor between unique small frequency-dependent slow conduction zones in all atrial regions in both atria. The slow conduction zones have been found to be myocyte bundle nodal points that correlate with fibro-fatty regions and rotational activity. It was further found that pulmonary vein isolation leads to beneficial remodeling by reducing slow conduction and reentries in nearly all atrial regions in both atria remote to the pulmonary veins.

As discussed in more detail below, the new polygon model leads to a disruptive understanding of the electrophysiological and structural mechanisms in AF, which may result in optimized AF treatment strategies. This newly developed reentry detection method can be used to improve the accuracy of atrial fibrillation driver detections. Additionally, AF therapies targeting regions of high myocyte bundle nodal points, fibro-fatty regions, and slow conduction may improve the treatment success rates. The data also provides a fundamental understanding of why pulmonary vein isolation has beneficial effects in regions remote from the pulmonary veins.

The present work aimed to determine electrophysiological characteristics both in a human-like large animal AF model and in AF patients that may facilitate the occurrence of local arrhythmias. Mapping studies have aimed to test the hypothesis that AF is caused by either focal or reentrant drivers in AF using atrial electrograms (AEGs) based on sequential or simultaneous multisite site mapping at the endocardium and epicardium using different types and numbers of electrodes. Several studies showed that reentry circuits can drive AF and that slow conduction leads to reentry in AF. Although the overall association between areas of slow conduction and AF drivers is evident, several issues remain unsettled including: i) whether there are sub-regional differences in reentrant/rotational activities and slow conduction within the left and right atrium, ii) whether there is a critical activation delay threshold that helps differentiate tissue that produces stable reentry as compared to the tissue that does not support stable reentry, iii) what is the shape of the reentrant trajectory based on high-resolution mapping, iv) whether reentrant/rotational activities correlate with slow conduction zones and substrate characteristics, v) the effects of PVI on reentrant/rotational activities and slow conduction zones in regions remote to the pulmonary veins, and vi) whether reentrant/rotational activities and slow conduction characteristics are similar in a rapid atrial pacing (RAP) model of AF and in patients with persistent AF. As discussed below, the studies described herein aimed to answer these questions in a canine model and patients of persistent AF.

To conduct the study, the inventors induced AF in 18 hound dogs by rapid atrial pacing (600 beats/min) for 3-8 weeks. In 5 dogs, the inventors also performed PVI. Before all the procedures, animals were premedicated with acepromazine (0.01-0.02 mg/kg, Vedco) and induced with propofol (3-7 mg/kg, Zoetis). All experiments were performed under general anesthesia (inhaled) with isoflurane (1-3%). Adequacy of anesthesia was assessed by toe pinch and palpebral reflex. For pacemaker insertion, the right jugular vein was accessed by direct cutdown and ligated distally. A bipolar screw-in Medtronic pacing lead was inserted through an incision in the right jugular vein. The tip of the lead was fluoroscopically placed and fixed in the RA appendage after confirming an adequate capture threshold (<0.5 mV with a pulse width of 0.4 ms). The proximal end of the pacing lead was connected to a custom-modified Medtronic programmable pulse generator that was subsequently implanted in a subcutaneous pocket in the neck. After all the incisions were closed, the dogs were allowed to recover from anesthesia and were returned to the animal quarters. After confirming an adequate threshold for atrial capture (<0.5 mV with pulse width 0.4 ms), rapid atrial pacing was performed incrementally over 1-3 days until adequate capture was confirmed at 600 bpm. The pacing was continued for 3-6 weeks until persistent AF was induced.

High-Density Mapping During Open Chest Surgery: Atrial epicardial mapping studies were performed during open-heart surgery during AF on the beating heart. High-resolution mapping was performed with the UnEmap mapping system (the University of Auckland, Auckland, New Zealand) which includes a triangular mapping plaque and records 117 bipolar electrogram signals (1 kHz sampling rate, 117 electrodes, interelectrode distance of 2.5 mm) covering a total area of 7.3 $cm^2$. The electrodes were placed on the atrial epicardial surface for recording. The interelectrode distance between each bipolar electrode was 2.5 mm. Bipolar electrograms were recorded from 6 different regions in both atria: posterior left atrium (PLA), left atrial free wall (LAFW), left atrial appendage (LAA), posterior right atrium (PRA), right atrial free wall (RAFW), right atrial appendage (RAA). Data were digitally recorded and processed with the UnEmap mapping system software and data were transferred in real-time, and stored on a personal computer for further analysis. The AF signal characteristics including Dominant Frequency (DF), Organization Index (00, Fractionation Interval (FI), Shannon's Entropy (ShEn) were calculated with in house MATLAB programs. Data were collected with the GE Prucka Cardiolab system (GE Healthcare), and two rectangular mapping plaques with 12 electrodes (3×4 electrodes, interelectrode distance 5 mm). The inventors excluded electrodes (<10%) with inadequate quality due to noise or poor contact.

Sequential activation maps of persistent AF were constructed for 10 consecutive seconds in each atrial region in all hearts. Data were analyzed automatically for activation times using an in house MATLAB programs by detecting the steepest negative slope in the bipolar electrogram. The advantage of bipolar electrograms is that bipolar atrial electrograms are sharper than unipolar electrograms and the differentiation of electrograms promotes the high-frequency components in the signal recordings. In alternative embodiments, different hardware, thresholds, values, and/or techniques may be used.

The electrogram measurements include cycle length (CL), dominant frequency (DF), organization index (OI), fractionation interval (FI), Shannon entropy (ShEn), detection of slow conduction regions, detection of rotational activity. The CL was calculated with the steepest negative slope using the maximal negative slope of the bipolar electrogram. The DF has been shown to correspond to rotational activity in AF. Dominant frequency was calculated with the highest power in the power spectrum using the fast Fourier transform and bandpass filtering with cutoff frequencies of 40 and 250 Hz. The OI is a frequency domain parameter of the temporal organization or regularity. Organization index was computed as the area under 1-Hz windows of the DF peak, and the next 3 harmonic peaks divided by the total area of the spectrum from 3 Hz up to the fifth harmonic peak. Fractionation Interval (FI) is the mean interval between deflections detected in the bipolar signal segment. Deflections were defined with the following conditions: (a) the bipolar peak-to-peak amplitude was greater than a defined noise level, (b) the time between a neighbored positive peak and the negative peak was within a 10 ms window, and (c) the detected deflection did not overlap within 50 ms with another detected deflection. The noise level was determined by the amplitude level, which avoids the detection of noise-related deflections in the iso-electric portions of the signal.

Shannon entropy (ShEn) is a measure of the complexity of the EGMS. Amplitude values of each EGM segment (3908 or 4000 amplitudes, 1 kHz, or 977 Hz sample rate) were calculated and these were binned into 1 of 29 bins with a width of 0.125 SDs. ShEn was calculated using the following formula, with p, the probability of an amplitude value occurring in bin i:

$$ShEn = \frac{-\sum_{i=1}^{29} p_i \log_{10} p_i}{\log_{10} p_i}.$$

Regarding detection of slow conduction regions, it is noted that conduction velocity cannot be measured from epicardial mapping alone as it may not include the entire pathway of the wavefront between 2 points. The inventors, therefore, used the term epicardial activation delay to describe this measure. To quantify changes in epicardial activation delay objectively and reproducibly, all electrogram data including its geometric coordinates were imported into MatLab (MatLab, Mathworks, Natick MA), and a proprietary code was written for automated calculation of epicardial activation delay. To correlate epicardial activation during AF, the epicardial maps were partitioned into small and fixed regions of interest (ROIs) of 2.5×2.5 mm, and the activation delay in each ROI during AF was automatically measured.

The proposed system was also used for robust detection of rotational activity. In the literature, the trajectory of reentries is calculated based on phase singularities. However, this method has several limitations for robust detection and can falsely detect phase singularities in the absence of rotors. In the present work, a completely new method was developed to detect the trajectory of rotational activity more robustly. Reentry was detected based on activation time maps showing 360-degree rotations, using both earliest and latest activation x,y-locations in the activation time maps over time. Multiple activation time maps were calculated in 5 ms steps over a time period of 10 seconds. In each of these local activation time maps the position of the earliest activation and the position of the latest activation was marked. If these detected locations of earliest and latest activation correlated over time with repetitive patterns showing loops, these activation patterns were considered as rotational activities. The proposed algorithm also detects slow conduction zones and activation delay along the reentry trajectory of the earliest and latest activation. Reentry stability was defined as the duration of observed reentrant activity over time. Additional manual annotation of 360°-rotations in local activation time maps confirmed the automatic detections. The inventors further assessed the accuracy of the reentry detection methods by comparing the phase method which focuses on the reentry core and the new developed method based on the earliest and latest activation with the ground truth in the manual annotations. Accuracy was defined as measure how often the algorithm classifies a reentry correctly.

The computer program was written in a proprietary code in MatLab (MatLab, Mathworks, Natick MA). The reentry stability was assessed as the duration of observed reentrant activity over time. Additional manual annotation of 360-degree rotations in local activation time maps was used for confirmation of the automatic detections of rotational activities. In addition to reentries, focal activities were also automatically detected. Focal activities were detected as instantaneous earliest activities within activation time maps in 5 ms time steps. In alternative embodiments, different time steps may be used.

In the open chest model, pulmonary vein isolation was performed on the epicardium with an isolator synergy ablation clamp (AtriCure Synergy, AtriCure, Inc., Cincinnati, OH) for bipolar radiofrequency energy lesions. The Atricure system includes a bipolar RF clamp and an RF generator. Lines of conduction block were generated by RF energy delivery (75 volts, 750 milliamps) to tissue compressed between the jaws of the clamp. Energy delivery was continued until the lesion was transmural, indicated by steady and reduced conductance between electrodes in the clamp. Post PVI epicardial mapping was performed again in the bi-atrial regions with the high-resolution mapping plaque.

The inventors also performed tissue section analysis in 6 animals. After the open chest epicardial mapping procedure, the heart was excised out of the chest and immersed in an ice-cold cardioplegia solution containing (mmol/l) NaCl 128, KCl 15, HEPES 10, $MgSO_4$ 1.2, $NaH_2PO_4$ 0.6, $CaCl_2$ 1.0, glucose 10, and heparin (0.0001 U/ml); pH 7.4. The solutions were equilibrated with 100% 02. The inventors then cannulated the heart via the aorta and perfused with ice-cold cardioplegia solution containing protease inhibitors (Millipore Sigma, P8340) until the vessels were clear of blood, and tissue was cold. The six mapped bi-atrial tissue regions in the size of the triangular mapping catheter were dissected. Specimens from 4 dogs were fixed in 10% formalin and embedded in paraffin for further examination.

Paraffin sections with 5 µm thickness were stained using Masson's Trichrome stain kit (Sigma). Paraffin was then removed in Xylene for three minutes twice and then in the mixture of 100% Xylene and in absolute Ethanol for three minutes twice. Sections were then rehydrated with ethanol series which include in absolute Ethanol (twice), 95% Ethanol, 70% Ethanol, and 50% Ethanol. The paraffin sections were treated with Bouin's mordant at room temperature overnight. The following day the sections were rinsed in running water to remove excess yellow. The sections were stained in Weigert's Iron Hematoxylin solution for five minutes. They were washed under running water for 5 minutes and briefly rinsed in distilled water. The sections were also stained in Beibrich Scarlet-Acid fuchsin for 5 minutes, followed by a rinse in distilled water. Subsequently, the sections were incubated in the phosphomolybdic-phosphotungstic acid solution for 5 minutes. The issue section was then stained in the Aniline Blue solution for 5 minutes. The sections were incubated in 1% Glacial acetic acid for 2 minutes. The sections were then dehydrated through ethanol series, which include 70%, 90%, and absolute Ethanol (twice). Then, the sections were placed in Xylene 5 minutes twice. A coverslip was finally placed using cytosol mounting media on the sections for microscope examination.

Masson's trichrome stained tissue sections at different depths (0, 200, and 500 µm) from the epicardial surface were digitized with the NanoZoomer 2.0-HT at 5× magnification. The whole sections were divided into quadrant by drawing regions of interest for the quantitative morphometric analysis. The inventors quantified uniformity of fiber orientation in RAP atrial tissue sections at 200 µm and 500 µm from the epicardial surface and quantified the orientation of the myocytes. The standard deviation of the detected fiber angle and number of fiber crossing points were quantified in ROI's of 2.5 mm×2.5 mm similar to the electrode sizes of the Unemap mapping plaque using the ImageJ plugin OrientationJ and fiber crossing were defined as angle >30 degree between neighbored ROI's (compare Supplemental Data S45-50). The inventors further analyzed the degree of focal fibrosis in Masson's trichrome stained tissue section at 200 µm levels with semi-automatic color-based segmentation and the degree of interstitial fibrosis as there was qualitative similarity among sections at different depths using ImageJ and macro.

The inventors evaluated slow conduction in reentry circuits and focal sources using the high-definition (HD) mapping catheter with 16 equidistant electrodes (HD Grid Mapping Catheter Sensor Enabled, Abbott Technologies, Minneapolis, MN) in the LA in 4 persistent AF patients. The number of detected reentries and number of focal sources were also analyzed. The inventors further assessed the maximal activation delay at reentries and maximal activation delay at focal sources in ROI-sizes of 2.5 mm×2.5 mm, similar to ROIs in the animal model.

Regarding statistics, continuous variables with normal distribution are reported as mean and SD. For those with non-normal distribution, range and median are reported. For comparisons of continuous variables, a 2-sample t test with unequal variance was used if data were normally distributed and a Wilcoxon rank-sum test was used for non-normally distributed variables. For comparisons of multiple variables, 1- or 2-way ANOVA methods were used. Correlation between continuous variables (stability of rotational activities and electrogram measures) was evaluated using linear regression. The normality assumption was tested using the skewness and kurtosis test. A P value <0.05 was considered statistically significant. Analyses were conducted using STATA SigmaPlot 14.0 software (Systat Software, Inc., CA, USA) and MatLab (Mathworks, Natick MA).

A total of 18 hound dogs underwent electrophysiological study in AF. During AF, multiple rotational activities of different cycle lengths (103±13 ms, median 103 ms) were present in both atria in all 18 hearts. The rotational activity was detected in all regions (32 per heart, 5±2 per region, median 4) with stability over 424±505 ms. (median 270 ms, range 120-4940 ms). The locations of all reentry sites are summarized herein.

Rotational activities were detected in all six bi-atrial regions (i.e., in all regions in both atria). The location of mapping plaque in the six bi-atrial regions was determined, and multiple rotational activities in high-density local activation time (LAT) maps in all six atrial regions in heart #10 were identified. In this heart, the highest stability of rotational activities was detected in the RAA and second in the PLA. Rotational activities, which are AF drivers, were significantly faster in the PLA (94±7 ms, median 93 ms) and LAFW (96±5 ms, median 95 ms). Shortest CL was detected in the PLA in 47%, in the LAFW in 33%, in the PRA in 13%, and in the RAA in 7% of all animals. In contrast, the longest CL was in the RAA in 90% and in the RAFW in 10% of all animals.

The stability of rotational activities in the different regions of the heart was also considered. Percentage of rotational activity time episodes vs total mapping time in all regions was calculated, and it was determined that the average of rotational activity episodes covered 12% of the total mapping time in the RAA. Rotational activities were most stable in the RAA (405±219 ms, median 420 ms) and second in the posterior left atrium (PLA) (267±115 ms, median 300 ms). The highest stability of rotational activity was detected in the RAA in 80%, in the RAFW and LAFW in 10% of the animals. The second most stable reentries were detected in the LAA in 60% and in the RAFW in 40% of all animals. Importantly, rotational activity was most present in the RAA in 12% (average) of the mapping time, second in the RAFW and third in the PLA of the mapping time.

Multiple interacting rotational activities in all regions in both atria were also analyzed, and local activation time maps showing the stable reentrant circuit in the RAA were generated to mark the earliest activation and the latest activation. Data from a representative example of AF attributable to activation from the stable reentrant site in the RAA (from heart #1) was considered. The reentrant trajectory of 2 loops of earliest and latest activation was identified, along with slow conduction zones at the edges of the trajectory of earliest and latest activation. The data indicates reentrant circuit trajectory along with patterns of lines (up to 6 mm in panel with curvature angle between the lines and >4 times slower conduction at edges in propagation (highest curvature angles)). Conduction patterns are potentially due to patterns in fiber directions. Reentrant circuit trajectory of a circular reentry was considered, in addition to redefined reentrant circuit trajectory along with patterns of lines and with curvature angle between the lines at >4 times slower conduction at edges in propagation. The conduction pattern lines are potentially due to patterns in fiber directions.

Heart #10 was a representative example of AF activation showing stable rotational activities in all six bi-atrial regions in the same animal. The rotational activities during AF anchored frequently at slow conduction zones (number n>=3) of activation delay (14.9±5.2 ms, median 13.0 ms, range 10-35 ms) over a distance of 2.5 mm. In contrast-to phase singularity analysis of reentry in previous reports, the inventors defined the trajectory and anchoring of rotational activities based on activation and activation delay in high-resolution mapping data. An oval shape schematic of a reentrant circuit trajectory is typically described in the literature. In contrast, high density mapping shows that the trajectory of reentry was different with patterns of lines with normal conduction and slow conduction at the edges of these line patterns. As discussed in more detail below, the observed curvature angle was 138° between these propagation lines. Activation time at the edges of the reentrant trajectory (15±5 ms, median 13 ms) was four times slower compared to the straight and fast conduction at propagation lines with activation delay (4.1±2.0 ms, median 4.0 ms). These detected slow and highly curved conduction regions measured >2.5 mm×2.5 mm and were stable over time. Both trajectories of earliest and latest activation within activation time maps over time had the same overlapping slow conduction regions. Slow conduction zones are located at abrupt changes in the fiber direction. The highest activation delays were found in the regions LAA, RAFW, and RAA, and were zones of low peak-to-peak voltage <1 mV.

The episodes necessary for the induction of a stable reentry based on high-resolution mapping were initially unclear. The initiation and maintenance of rotational activity between small slow conduction zones were explored, and the development stages of rotational activity over time were identified. The development states were based on varying activation pattern episodes in Heart #7 in the region RAA, as follows: 1) focal wave activation (1800-1830 ms, and further LAT maps of repetitive focal wave activation (600-1830 ms) was also used), 2) first instable reentrant loop (1860, 1890 ms), 3) chaotic activations (1920-2010 ms), and 4) stable rotational activity (2040-3870 ms). Activation time maps, trajectory, and activation delay of earliest activation time in 2 reentrant loops were also generated.

A representative example (heart #7) of the development stages of rotational activity over time including varying activation pattern episodes in the region RAA was considered. The first episode is a repetitive planar wave activation (0-570 ms). Then a time episode of repetitive focal wave activation (600-1830 ms) continues, which importantly induce a first instable reentrant loop in 1860 ms and 1890 ms. Importantly this reentrant loop resulted in chaotic activations over 210 ms at multiple slow conduction zones (time 1920-2010 ms), which then induced stable rotational activity (2070-4470 ms). The activation time maps, trajectory, and activation delay of earliest activation time in 2 reentrant loops of this stable reentry were determined. The inventors further characterized these slow conduction regions which are responsible for the anchoring of reentrant drivers.

Activation delay over time in 8 following reentrant loops was considered, along with activation delay in the six different regions in reentrant loops of all animals. Importantly, it is noted that activation delays in reentrant loops were similar in all bi-atrial regions, but most activation delay zones (>10 ms) delay were detected in the PLA.

Episodes of stable reentries were frequently observed. However the reason for abrupt ending of reentries in high resolution mapping initially remained unclear. The inventors therefore analyzed the CL variations during and before the termination of stable reentry. It was found that in stable reentry (2 seconds), spontaneous increases in CL occurred before the termination of the rotations. Termination of rotational activity because of CL prolongation and similar slow conduction zone locations in AF and SR was analyzed to obtain a representative example of cycle length variation and the termination of stable reentry. It was shown that an increase in CL from 120 ms to 150 ms terminated the stable reentry and then lead to planar wave activation. Activation patterns in AF are complex. In this study, episodes of different activation patterns including rotational, focal activity, complex activation pattern, and normal nearly planar wave activations varied over time in the same region. For heart #10, (1) CL of 120 ms changed to (2) CL of 150 ms after 1.5 seconds rotational activity, and after CL prolongation (3) rotational activity abruptly ended.

Rotational activity (CL=90 ms) in LAT maps (30 ms steps) in the RAA in heart #10 was also studied. The heart exhibited an episode of rotational activity, and a more organized nearly planar wave episode in the same region (RAA) and animal. Slow conduction at the same location during rotational activity and planar wave activation was also identified. Importantly, the zones of slow conduction during the reentrant activity were at the same locations also present during planar wave activation and during sinus rhythm.

Overlapping slow conduction zones during AF and during sinus rhythm in the PLA were also considered. Activation delay increased by the factor 3-4 during AF compared to sinus rhythm or planar wave activation at slow conduction zones. CL increased from 120 ms to 150 ms (compare signal recordings). It was determined that cycle length variation was highest in the RAA. Also identified was an exponential decrease of activation delay during AF with increasing CL and increasing pacing intervals (200 ms to 400 ms). Pacing was performed from the LAA.

The activation patterns focal activity, epicardial breakthrough, and line of block were reported in previous studies in high-density epicardial AF mapping. In this study, the inventors further found a new activation pattern, referred to as 'thin line activation.' Thin line activation is defined as simultaneous earliest activation along thin line regions on the epicardial surface. Importantly these thin line activations often resulted in activation patterns such as focal activity and line of block activation.

Focal activity as simultaneous activation between lines of block was found, and locations were consistent over time episodes in LAT maps. Focal activities between line of blocks (up to 25 mm) were frequently observed at the same locations potentially because of simultaneous activation in fiber lines. Figure of eight activation along activation lines in the PRA in heart #5 was also frequently observed at the same location. The size of the figure eight reentrant part is 3 mm×6 mm. Additionally, focal activities between the line of blocks were frequently observed at the same locations. Most figure-of-eight-activations with small circuit dimension were located in the PLA.

The inventors further analyzed the underlying substrate characteristics in all bi-atrial regions in 6 animals. Specifically, the substrate characteristics and correlation of rotational activity with fiber crossings density and electrogram measures were analyzed. Masson's trichrome stained tissue sections in the six bi-atrial regions: left atrial appendage (LAA), posterior left atrium (PLA), left atrial free wall (LAFW), posterior right atrium (PRA), right atrial appendage (RAA), right atrial free wall (RAFW) were considered. It was found that dense focal fibrosis developed at fiber crossings, and it is noted that focal fibrosis/fat was located in 90% of the cases at fiber crossings.

The highest focal degree of fibrosis/fat was detected in the PLA (49±14%, median 42%) in the LAFW (47±19%, median 50%). The highest anisotropy was detected in the PLA, LAA and in the right atrium in the RAA (P value non-significant). It was also determined that the highest number of fiber crossings were present in the RAA, LAA, and PLA regions. Importantly, the stability of rotational activity correlated with the number of fiber crossings (R=0.6, P<0.05). Furthermore the slow conduction regions were fibrotic/fat tissue regions in histological tissue sections (>=3 mm) and low voltage regions (<1 mV). Correlation of electrogram measures with stability of rotational activity was performed in the order of the highest correlation to less correlation.

The inventors further correlated different established electrogram measures with detected stability of rotational activity. Importantly, stability of rotational activity correlated with electrogram measures OI (R=0.68), FI (R=0.61), ShEn (R=0.58) and CL (R=0.56), but not with DF (R=0.28), p<0.0001, for all comparisons. The stability of rotational activity correlated best with DI. Detailed AF EGM values of the EGM measures CL, OI, FI, ShEn, DF in each region, and in each individual animal were also determined.

To assess the beneficial effects of PVI on AF, the inventors performed epicardial pulmonary vein isolation in 5 hearts. PVI led to a significant increase in cycle length (range: 2.3%-14.1%). The PVI led to a significant increase in CL in nearly all regions remote to the PVs, and the stability of rotational activity decreased significantly (baseline vs after PVI) in nearly all atrial regions. It was also determined that slow conduction zones were similarly located pre and post PVI. Reduced slow conduction zone/block was found after PVI.

The inventors evaluated slow conduction at reentry sites and focal sources near the pulmonary veins in 4 patients using the high-definition (HD) mapping catheter with 16 equidistant electrodes (HD Grid Mapping Catheter Sensor Enabled, Abbott Technologies, Minneapolis, MN). Clinical left atrial evaluation of AF drivers and slow conduction zones in persistent AF patients was conducted using an HD-grid catheter with 16 electrodes (interelectrode distance of 2.5 mm) in accordance with an illustrative embodiment. The system used 24 bipolar signal recordings between the 16 electrodes of the HD grid catheter. Similar to the findings observed in the rapid atrial pacing model in animals, high activation delay occurred at edges of the reentrant circuits.

An activation time map showing a reentrant circuit showing increased activation delay at one trajectory segments (3 mm) was generated. The activation time map near the PV indicates a reentrant circuit with the 2 to 6 fold higher activation delay at one edge of the reentrant trajectory compared to the other trajectory segment parts. The inventors detected 2.3±1.6 (median 2) reentries and 2.1±1.1 (median 2) focal sources per cycle in patients in the left atrium. The number of simultaneous activations per cycle was 2.0±1.5 (median 2). Importantly, maximal activation delay at reentries was 35±17 ms (median 30 ms) which is about 2× higher compared to the rapid atrial pacing model. Maximal activation delay at focal sources was 51±20 ms (median 53 ms) along 2.5 mm.

The inventors thus considered whether reentries frequently anchored between slow sonduction zones in all bi-atrial regions. A detailed analysis of the rotational activity in both atria, including the appendages based on high-resolution contact mapping was not previously studied. The present results demonstrated that persistent AF drivers were maintained by activation wavefronts emanating from interacting rotational and focal activity in all six analyzed bi-atrial regions, and that they likely acted as drivers. Rotational activity automatically detected with the new algorithm based on the earliest and latest activation was most stable in the appendages and PLA, and it was anchored between small slow conduction zones with activation delay >10 ms. The inventors also observed changing beat-to-beat wavefronts and varying spatiotemporal behavior of driver activities. Reentrant activation was not sustained (median, 2.6 rotations lasting 449±89 ms), but meandered and recurred repetitively in the same region between (n>=3) small slow conduction zones.

Several previous studies showed PV-triggers and that AF triggers outside the PVs were located in the vena cavae, the crista terminalis, the coronary sinus, the ligament of Marshall, the inter-atrial septum, and the appendages. The role of the PVs in the development and maintenance of AF has been explored. Focal and rotor activity has also been detected with spatial stability using low-resolution endocardial basket catheter and phase singularity AF mapping. A noninvasive mapping study in paroxysmal and persistent AF patients identified multiple (2-5) concurrent wavelets (92%), with both simultaneous focal activation from areas near the pulmonary veins (69%) and non-pulmonary veins (62%), but reentry which sustained >1 rotation was rarely seen. In contrast, AF drivers in a noninvasive mapping study resulted in 80.5% reentries and 19.5% focal breakthroughs with incessantly changing beat-to-beat wavefronts and spatiotemporal behavior.

However, in the present study, the inventors clearly found stable rotational activities before and after PVI in the RAA and also in the LAA in which AF drivers were more stable compared to most other regions. Based on the findings in this work, electrical isolation of the appendages in addition to PVI can be used to further improve the success rate of freedom from AF compared to PVI only. A previous clinical study showed that the left atrial appendage may be an underrecognized trigger site of atrial fibrillation. Furthermore, it has been shown that empirical electrical isolation of the left atrial appendage improved long-term freedom from atrial arrhythmias. In a comparison of the present study, the finding of rotational driver activation during AF is in line, in whole or in part, with the findings of others. However, importantly, the present data further characterized AF drivers with slow conduction regions.

As discussed in more detail below, the inventors also examined the structural and functional polygon reentry model of anchored reentry between fiber crossings. It was demonstrated that the reentrant circuit trajectory were more complex than circles or ovals like those previously described and followed line patterns with a curvature angle between lines, which were partially structural fiber lines in histological tissue sections. The velocity of stable rotational activities along the described line patterns with curvature propagation angle was 4× slower at the edges of the trajectory compared to the propagation along the fiber lines. These slow conduction zones were crossing fibers, fibrosis, or fat tissue zones in the histological tissue section analysis. In this study, focal fibrosis regions were located at fiber crossings in 90% of the focal fibrosis zones. Focal fibrosis may develop at fiber crossings. Especially in the PLA near the pulmonary veins and in the LAFW dense focal fibrosis developed at zones of fiber crossings. Furthermore, the stability of rotational activity correlated with the number of fiber crossings. It has been suggested that fiber orientation distribution is an important factor in the development of AF. In this study, the inventors detected a trend between fiber orientation distributions measured with the standard deviation of fiber orientations and stability of rotational activity. In contrast to previous studies, the inventors analyzed for the first time the number of fiber crossings in different bi-atrial regions. Importantly, the number of fiber crossings were more specific and clearly correlated with the stability of rotational activity.

It has been demonstrated that main contributors to conduction and slow conduction in the heart are: a) fiber orientation, b) Na channel characteristics, c) Gap junction characteristics, and d) presence of fibrosis. It has also been demonstrated that conduction delay occurs at zones that reveal sudden changes in the fiber direction. These studies also show an abrupt increase in axial resistivity in the direction of propagation ensued, which may result in a decrease of the safety factor for propagation. It has further been demonstrated that zones of activation delay of up to 120 ms over distances as small as 3 mm in canine pulmonary veins correlated with abrupt changes in fascicle orientation. The architecture of muscular sleeves in the PVs may facilitate reentry and arrhythmias associated with the ectopic activity. In this RAP animal model, activation delay up to 39 ms, within 2.5 mm×2.5 mm was >4 times larger compared to normal activation and activation frequently curved around slow conduction zones, which predisposed to reentry. In humans, reentries and focal sources anchored at zones of activation delays up to 90 ms within 2.5 mm using the HD grid catheter near the PVs. Furthermore, these findings are in line with observations from others, who have shown that stable reentries anchored at regions of increased fiber angle (epicardial 37 degree) and interstitial fibrosis (12.8±1%) and made repetitive a U-turn at micro-anatomic tracks (2 mm). The present findings of slow conduction sizes and activation delays are also similar to observations from others. Furthermore, the inventors have discovered slow conduction regions and anchored reentries around these slow conduction regions in all six analyzed bi-atrial regions.

The reentry models of circus movement, leading circle, and spiral wave were considered in comparison to the new proposed model of reentry along line patterns in the form of a polygon. In the circus movement reentry model, the anatomic reentry is around a fixed obstacle and allows for an excitable gap. In the leading circle reentry model, the conduction velocity (CV) and refractory period (RP) determine the circuit size. In addition, the center of the circuit is maintained refractory by centripetal wavelets. The spiral wave model describes a curved wave front with a core, and the so called phase singularity (PS) rotates around an excitable but unexcited core. In contrast to the previous models, the proposed model describes both structural and functional characteristics with slow conduction zones at the edges of propagation line patterns. Previous models focused on the tip of the rotational activity analyzing the core with phase singularity points in phase maps. In contrast, the focus in the proposed model is the earliest and latest activation over time and slow conduction determined with activation delay within activation time maps.

The analysis shows that conduction zones (>3 mm) may be zones of fiber crossings in all bi-atrial regions. At these fiber crossings zones, focal fibrosis and fat tissue was detected and may develop over time at these zones. These fiber crossing zones were frequency dependent zones of activation delay, and rotational activity anchored between these zones. These zones were further located at the same locations in different rhythms or activation patterns (AF and sinus rhythm, rotational activity and planar wave activation). Importantly, activation delay increased at these zones during rotational activity and decreased during planar wave activation or sinus rhythm. PVI increased CL and reduced the activation delay of these zones in all regions remote to the PVs. These activation delay zones at rotational activities were present in the animal model and in patients. Importantly, these findings result in a proposed new model of reentry. In contrast to the previous models, the new model describes both structural and functional characteristics with slow conduction zones at the edges of propagation line patterns. Previous models focused on the tip of the rotational activity analyzing the core with phase singularity points in phase maps. The focus in the new proposed system is to model the earliest and latest activation within activation time maps.

The above-discussed data helps define a new paradigm for the mechanism that induces and maintains persistent AF. Understanding the mechanism of reentry between small slow conduction regions presents opportunities for new potential approaches to the treatment of persistent AF, especially for ablation. In previous reports, the trajectory of reentries was calculated based on phase singularities. But, this method is limited in robust reentrant detection and can falsely detect phase singularities in the absence of rotors. In contrast, the proposed system presents a completely new method for detecting the trajectory of rotational activity more robustly based on earliest, latest activation, and activation delay. This new method may be integrated into future clinical systems to provide physicians a robust detection of AF drivers in addition to relevant slow conduction regions. Current success rates in persistent AF have been far from optimal, and actual treatment approaches remain largely empirical because doctors have not understood well enough the mechanism(s) maintaining persistent AF. Study of the mechanism(s) maintaining AF has been limited by low resolution, and the difficulty in mapping this complex arrhythmia. The data from this work provides opportunities for a targeted, rather than an empirical approach to treat AF.

In summary, the high-density bi-atrial epicardial mapping study in hearts with persistent AF was conducted, and it was found that multiple interacting rotational activities in all bi-atrial regions maintained AF and their trajectories anchored between small frequency-dependent regions of activation delay. PVI led to beneficial remodeling in all regions remote to the PVs in the LA and RA. These data can be used to identify a new paradigm for persistent AF.

Polygon Reentry Model Paradigm

Additional experiments further assessed above-mentioned polygon reentry model for AF, which describes for the first time both structural and functional mechanisms based on a reentry detection algorithm tracking the earliest and latest activation. Specifically, the inventors performed high-density mapping of persistent AF in both 48 open-chest dogs (3-14 weeks rapid atrial pacing, 117 electrodes, 2.5 mm distance in six bi-atrial regions) and ten patients. In contrast to the historical circular reentry model, the new algorithm revealed that the reentry shape followed unique line patterns in form of a 'polygon' with slow conduction (defined as >10 ms per 2.5 mm) at the edges of these line patterns. The new algorithm automatically detected rotational activity in all six bi-atrial regions. The trajectory at the edges had four-fold slower conduction (activation delay 15±5 ms, median 13 ms) compared to the rest of the trajectory providing a unique anchoring mechanism critical for the emergence of stable reentry with the stability of 120-4940 ms, and highest stability in the right atrial appendage (RAA).

This new algorithm was 26% more accurate in reentry detection than previously established phase singularity methods. The new polygon reentry model is anchored in the substrate to macroscopic fiber crossings and fibrosis/fat. In the histological tissue analysis, slow conduction zones (>3 mm) corresponded to myofiber crossings/fibro-fatty infiltrations in all bi-atrial regions. The degree of dense fibro-fatty infiltrations correlated with slow conduction zones (R=0.8, P<0.01), and fiber crossing density correlated with the stability of rotational activity (R=0.6, P<0.05). It was found that these slow conduction zones have a unique response to the AF cycle length (CL) with two-fold higher CL in AF vs sinus rhythm (SR). Pulmonary vein isolation (PVI) was performed in five animals and led to an interruption of zones of slow conduction in the PLA. This led to reduced stability of rotational drivers not only in the PLA but also to slowing of rotational activity in all regions remote from the PVs. In patients with persistent AF undergoing AF ablation, mapping with the HD-grid-catheter (16 electrodes, 3 mm distance) revealed that activation delay at the reentrant trajectory was 2× higher at the trajectory edges with maximal delay 20.5±8.1 ms vs 9.3±8.8 ms (P<0.01) and 1.4× higher during AF 18.0±11.6 ms vs. SR/CS-pacing 13.0±18.7 ms (P<0.01).

Described in more detail below is the analysis of rotational activities based on this new algorithm anchored between small frequency-dependent slow conduction zones in all bi-atrial regions during AF. Using the new polygon model, one can better understand and determine the electrophysiological and structural mechanisms in AF. The analysis shows that reentry propagation follows unique line patterns in form of a polygon with slow conduction at the edges of these line patterns. Additionally, reentries frequently anchor between unique small frequency-dependent slow conduction zones in all bi-atrial regions. Slow conduction zones are myofiber crossings that develop into fibro-fatty regions over time and are anchor zones of rotational activity. It was further found that pulmonary vein isolation leads to beneficial remodeling by reducing slow conduction and reentries in nearly all bi-atrial regions remote to the pulmonary veins. The proposed new reentry detection method is more accurate than established phase methods.

The new polygon model leads to a disruptive understanding of the electrophysiological and structural mechanisms in AF, which may result in optimized AF treatment strategies. This newly developed reentry detection method also improves the accuracy of detecting atrial fibrillation drivers. Additionally, atrial fibrillation therapies targeting regions of high fiber crossings, fibro-fatty infiltration, and slow conduction may improve the treatment success rates. The analysis further provides a fundamental understanding of why pulmonary vein isolation has beneficial effects in remote regions to the pulmonary veins.

In this analysis, a total of 48 purpose hound dogs animals were studied, and five dogs were used as controls. The rapid atrial pacing model is described above. Atrial fibrillation was induced in 43 hound dogs by rapid atrial pacing (RAP) (600 beats/min) from the right atrial appendage for 3-14 weeks with a pacing lead and generator (Medtronic). All experiments under general anesthesia (inhaled) with isoflurane (1-3%) and RAP pacing after surgical recovery. FIG. 1 is a diagram illustrating parameters of the study in accordance with an illustrative embodiment.

On the beating heart, atrial epicardial high-resolution electrograms were collected during open-chest preparation in six bi-atrial regions. In each of the six bi-atrial regions, 117 bipolar electrogram signals (1 kHz sampling rate, 2.5 mm interelectrode distance) were recorded using the UnEmap mapping system (University of Auckland, Auckland, New Zealand). This triangular mapping plaque has the electrodes arrangement of 16 electrodes×13 electrodes and 15×12 bipolar electrode pairs, and covers a total area of 7.3 $cm^2$ on the atrial epicardial surface. In 10 second windows, bipolar electrograms were recorded in all animals at the same six regions including posterior left atrium (PLA), left atrial free wall (LAFW), left atrial appendage (LAA), posterior right atrium (PRA), right atrial free wall (RAFW), and right atrial appendage (RAA). For optimized analysis, electrodes with (<10%) with noise or poor contact were excluded. Later, cycle length, slow conduction, rotational activity, and electrogram measures were quantified including Dominant Frequency (DF), Organization Index (OD), Fractionation Interval (FI), and Shannon's Entropy (ShEn) with in-house Matlab (Mathworks, Natick MA) programs.

The inventors also performed a detailed slow conduction analysis in all bi-atrial regions. Conduction velocity cannot be measured from epicardial mapping alone, as it may not include the entire pathway of the wavefront between 2 points. Therefore, the term activation delay is used to describe this measure. To calculate changes in epicardial activation delay objectively and reproducibly, all electrogram data including its geometric coordinates was imported into Matlab and proprietary code was developed and used for automated calculation of epicardial activation delay. In alternative implementations, software other than Matlab may be used for the calculations. To correlate epicardial activation during AF, the maps were partitioned into small fixed regions of interest (ROIs) (2.5 mm×2.5 mm). The activation delay was automatically quantified in each region of interest (ROI) during AF and sinus rhythm/paced rhythm.

In previous studies, the trajectory of reentries was calculated based on phase singularities. However, this method can falsely detect phase singularities in the absence of rotors. The new proposed algorithm tracks locations of earliest/latest activation in 5 millisecond (ms) steps over time. In alternative embodiments, different time steps may be used, such as 3 ms, 4, ms, 6 ms, etc. If these detected locations correlate over time with repetitive patterns showing 360° rotation, the activation pattern is considered as reentry. Reentry stability is defined as the duration of observed reentrant activity over time. Additional manual annotation of 360° rotations in local activation time maps confirmed the automatic detections. The accuracy of the reentry detection methods was further assessed by comparing the new method and the phase method with the ground truth in the manual annotations. Additionally, activation delay and maximal activation delay were calculated in reentry trajectories and at focal sources. The focal activities were calculated as simultaneous earliest activities within activation time maps in 5 ms time steps.

In order to assess the effects of PVI on AF drivers and slow conduction, all atrial regions were mapped pre/post PVI in high-resolution. The pulmonary veins were isolated by radiofrequency energy applications on the epicardium with the isolator synergy ablation clamp (AtriCure Synergy, AtriCure, Inc., Cincinnati, OH). With the AtriCure system, lesion lines were generated on the atrial tissue compressed between the jaws of the clamp. To control the energy for transmural lesions, the energy delivery was continued until a steady and reduced conductance was achieved between electrodes in the clamp.

To assess the structural characteristics in the histological tissue sections in all six-bi-atrial regions, the inventors further performed a detailed tissue section analysis in six animals. The heart was cannulated via the aorta and perfused with cold (4° C.) cardioplegia solution containing protease inhibitors (Millipore Sigma, P8340) until the vessels were clear of blood. After that, the six mapped bi-atrial tissue regions were dissected in the size of the triangular mapping plaque. The specimens were then fixed in 10% formalin and embedded in paraffin for further examination.

After fixing the tissue, the paraffin sections were stained with 5-µm thickness using Masson's Trichrome stain kit (Sigma). To quantify the substrate characteristics, the Masson's trichrome stained tissue sections were digitized between 200 and 500 micrometers (µm) depth from the epicardial surface at 5× magnification with the NanoZoomer 2.0-HT (Hamamatsu Photonics. Hamamatsu Japan). For a detailed analysis, the whole sections were divided into quadrants. Dense fibro-fatty regions were segmented with the image-processing tool ImageJ (National Institutes of Health), and the degree (%) of segmented dense fibro-fatty infiltration areas compared to the total tissue section area was calculated.

Additionally, the inventors quantified the standard deviation of macroscopic fiber orientation in 2.5 mm×2.5 mm ROI's similar to the inter-electrode distances using the plugin OrientationJ. Importantly, the number of macroscopic fiber crossing nodal points in tissue sections were further assessed. These fiber crossing nodal points were defined as angle >30° between macroscopic fiber direction intersection lines of neighbored regions of interest.

With the goal of translating the findings from animal to human AF, ten patients with early persistent AF (persistent AF<1 year) presented for AF ablation were enrolled. The patients received conscious sedation or general anesthesia at the discretion of the treating physician. After obtaining access, the physician performed transseptal puncture across the interatrial septum using an SL1 (Abbott, Chicago, IL) or Preface sheath (Biosense Webster, New Brunswick, NJ) and Bayliss RF needle (NRG® Transseptal Needle, Baylis Medical). The physician gave intravenous heparin with an activated clotting time (ACT) goal of >300 s.

Using the HD-Grid (4×4) mapping catheter (Abbott Technologies, Minneapolis, MN), the left atrium was mapped in high-resolution. The EGMs were recorded and tagged according to the anatomic location in the left atrium (posterior wall, roof, lateral wall, septum) on the Ensite NavX mapping system® (Abbott Technologies, Minneapolis, MN). The electrograms (sample frequency 2 kHz) were filtered with a bandpass filter (30 to 300 Hz) and a 60 Hz noise filter.

For the statistical analyses, continuous variables were reported with normal distribution as mean and standard deviation (SD). For those with non-normal distribution, range and median values were reported. In addition, the normality assumption was tested using the skewness and kurtosis test. For comparisons of continuous variables, a 2-tailed t-test was used with an unequal variance if data were normally distributed and a Wilcoxon rank-sum test for non-normally distributed variables. In contrast, for comparisons of multiple variables, 1- or 2-way ANOVA methods were used. Specifically, the one-way ANOVA test was used, followed by the Bonferroni post hoc test for multiple comparisons with adjusted P values. In addition, the correlation between continuous variables was evaluated using linear regression using the Pearson correlation coefficient (R) and 95% confidence intervals. A P value <0.05 was considered to be statistically significant. The statistical analyses were conducted using STATA SigmaPlot 14.0 software (Systat Software, Inc., CA, USA) and Matlab.

As discussed, altogether, a total of 48 dogs and ten patients were analyzed. This included 43 AF and five sinus/paced rhythm hound dogs for the electrophysiological study. FIG. 2 is a table that summarizes overall patient and animal characteristics in accordance with an illustrative embodiment. In the table of FIG. 2, data are shown as mean±SD for continuous variables, and % for categorical variables. Abbreviations in FIG. 2 included: AF, atrial fibrillation; BMI, body mass index; EF, ejection fraction; LA, left atrium; and LV, left ventricle.

During AF, multiple rotational activities were detected in all bi-atrial regions in the individual hearts. Importantly, the rotational activity was detected in all regions (32 per heart, 5±2 per region, median 4) with stability over 424±505 ms (median 270 ms, range 120-4940 ms). The rotational activities were most stable in the RAA (405±219 ms, median 420 ms) and second in the posterior left atrium (PLA) (267±115 ms, median 300 ms). However, rotational activity was most prevalent in the RAA (lasting 11% (average) of the mapping time). The average cycle length of rotational activities was 103±13 ms (median 103 ms). Rotational activities were significantly faster in the PLA (CL 94±7 ms, median 93 ms) and LAFW (96±5 ms, median 95 ms) compared to other atrial sub-regions. The shortest CL was detected in the PLA in 47%, in the LAFW in 33%, in the PRA in 13%, and in the RAA in 7% of all animals.

These results are shown in FIG. 3. FIG. 3A shows a representative example (heart #10) of detected rotations activities in accordance with an illustrative embodiment. More specifically, FIG. 3A shows rotational activities in high-density local activation time (LAT) maps in all six atrial regions in animal #10. FIG. 3B illustrates how the highest stability of rotational activities was detected in the RAA and second in the PLA in accordance with an illustrative embodiment. FIG. 3C shows regional distribution of CL in accordance with an illustrative embodiment. FIG. 3D depicts cycle length increase with increasing distance to the pulmonary veins in the six bi-atrial regions in accordance with an illustrative embodiment.

The inventors also assessed the trajectory and anchoring of rotational activities based on the newly developed method using earliest and latest activation and activation delay. Importantly, the rotational activities frequently anchored at regions with a long activation delay (14.9±5.2 ms, range 10-35 ms) over a distance of 2.5 mm. The detected slow and highly curved conduction zones measured >2.5 mm×2.5 mm and were stable over time, detected with both the trajectories of earliest and latest activation within activation time maps. In fact, activation delay at the edges of the reentrant trajectory (15±5 ms) was four times slower compared to the straight and fast conduction at propagation lines with activation delay (4.1±2.0 ms). In contrast to the oval shape schematic of a reentrant circuit trajectory, historically described in the literature, the trajectory of reentry based on earliest and latest activation in high-density mapping was different with patterns of lines with normal conduction and slow conduction at the edges of these line patterns. A representative example of a new reentry trajectory in the shape of a polygon with observed curvature angle (i.e. 138°) between these propagation lines was found. Importantly, the accuracy of automatically detecting reentries increased from 71% to 97% using the newly developed method compared to the established phase method with manual annotation of reentries.

Figure 4A:
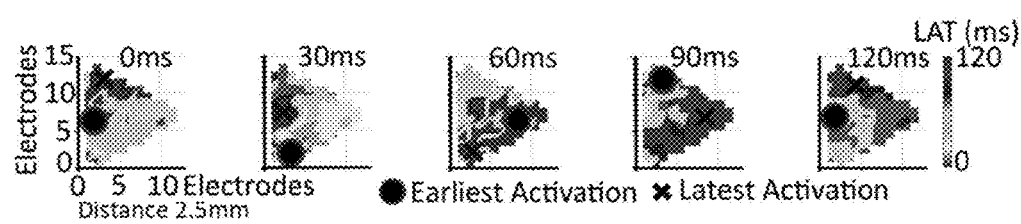
FIG. 4A depicts local activation time maps showing the stable reentrant circuit in the RAA in accordance with an illustrative embodiment.
Figure 4B:
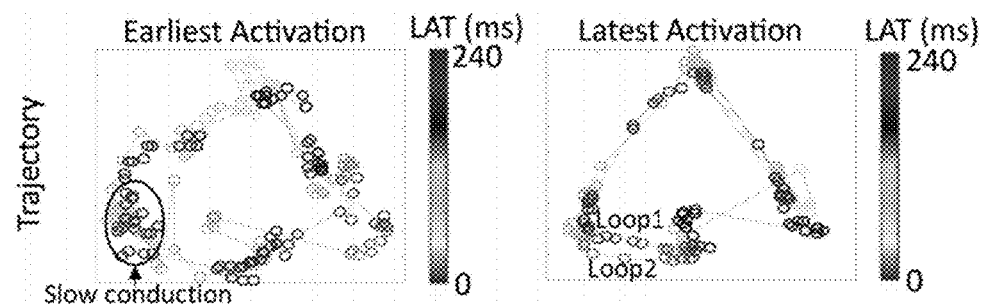
FIG. 4B depicts the reentrant trajectory of two loops of earliest and latest activation in accordance with an illustrative embodiment.

These results are shown in FIG. 4. FIG. 4A depicts local activation time maps showing the stable reentrant circuit in the RAA in accordance with an illustrative embodiment. The earliest activation is marked with a symbol: o, and the latest activation is marked with a symbol: x. The data shows a representative example of AF attributable to activation from the stable reentrant site in the RAA (from animal #1). FIG. 4B depicts the reentrant trajectory of two loops of earliest and latest activation in accordance with an illustrative embodiment. FIG. 4C depicts slow conduction zones at the edges of the earlies trajectory in accordance with an illustrative embodiment. Reentrant circuit trajectory follows line patterns (up to 6 mm), and the curvature angle between these lines had >4 times slower conduction compared to the straight line segments. FIG. 4D shows reentrant circuit trajectory of the historically circular reentry model in accordance with an illustrative embodiment. FIG. 4E shows the redefined reentrant circuit trajectory in the form of a polygon in accordance with an illustrative embodiment. FIG. 4F depicts the accuracy of detected rotational activity in the RAA based on previously described established phase singularity method (left) and on the completely new algorithm based on earliest and latest activation (right) in accordance with an illustrative embodiment. The accuracy, when compared to the ground truth using the manual detection, was 71% and 97% (right panel), respectively.

Figure 5A:
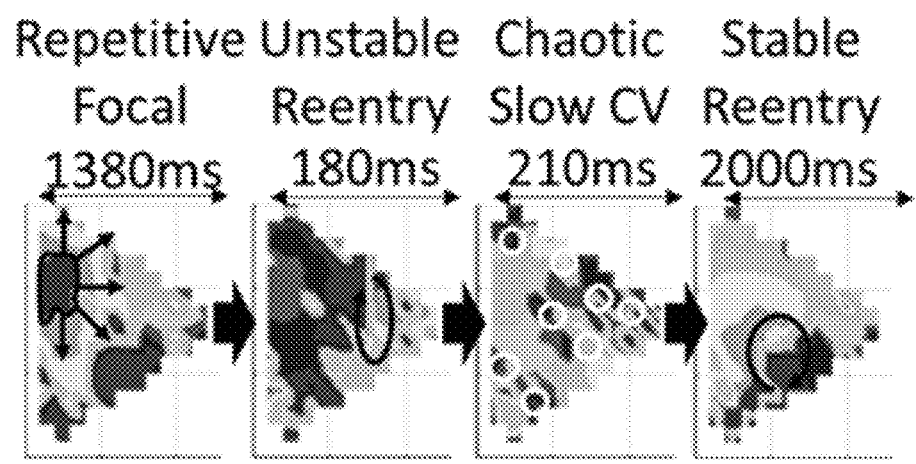
FIG. 5A depicts a representative example of the development stages of rotational activity over time consisting of varying activation pattern episodes in animal #7 in the region RAA in accordance with an illustrative embodiment.

The inventors further assessed activation patterns necessary for the induction of a stable reentry based on high-resolution mapping. FIG. 5A depicts a representative example of the development stages of rotational activity over time consisting of varying activation pattern episodes in animal #7 in the region RAA in accordance with an illustrative embodiment. The first episode is a repetitive planar wave activation. Then a time episode with repetitive focal wave activation continues, which induces a first unstable reentrant loop. This reentrant loop then resulted in chaotic activations with multiple small slow conduction zones, which then induced stable rotational activity over 2 seconds. The slow conduction zone values in following reentrant loops in all bi-atrial regions were similar over time. Focal wave activation had a duration of 1380 ms, the first unstable reentrant loop had a duration of 180 ms, the chaotic activations had a duration of 210 ms, and the stable rotational activity had a duration of 2000 ms.

Figure 5B:
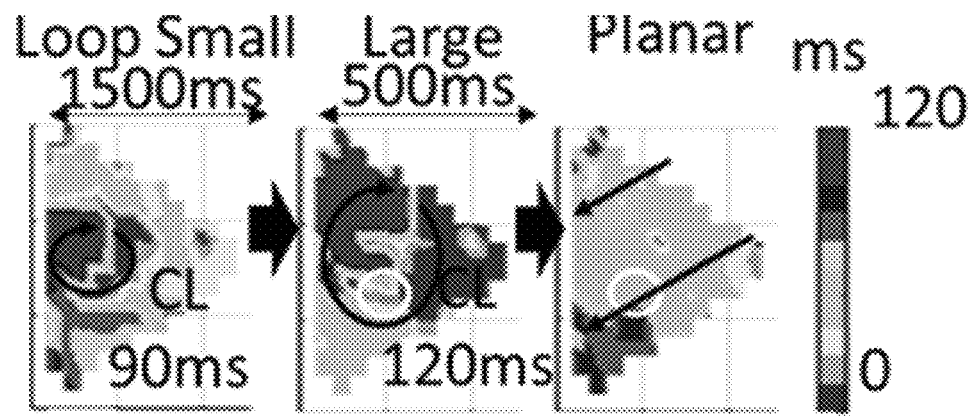
FIG. 5B is a representative example of cycle length variation and the termination of stable reentry in accordance with an illustrative embodiment.

In the present study, episodes of different activation patterns including rotational, focal activity, complex activation pattern, and normal nearly planar wave activations varied over time in the individual atrial regions. Therefore, the CL-variations were analyzed during and before the termination of stable reentry to assess the pattern of reentry termination using high-resolution mapping. It was found that in stable reentries, CL increased spontaneously before the termination of the rotations. FIG. 5B is a representative example of cycle length variation and the termination of stable reentry in accordance with an illustrative embodiment. In FIG. 5B, the reentry was stable for 2 seconds. After the rotational activity (1.5 s) with a small reentrant loop, the CL increased from 90 ms to 120 ms. After the reentry with a larger loop and larger CL, the reentry terminated and then resulted in a planar wave activation. Importantly, the zones of slow conduction during the reentrant activity in AF were at the same locations as slow conduction zones present during planar wave activation and sinus rhythm/paced rhythm.

Figure 5C:
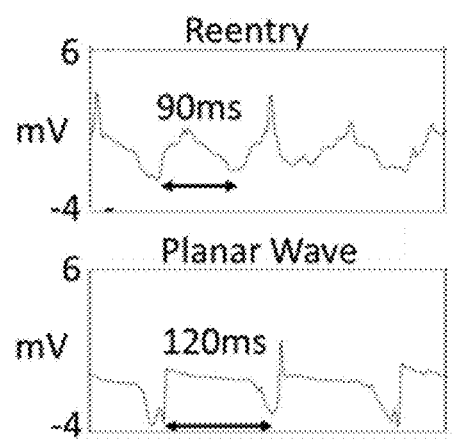
FIG. 5C shows bipolar signal recordings at reentry (CL of 90 ms) and more organized, nearly planar wave episode (CL of 120 ms) in the same region (RAA) and animal in accordance with an illustrative embodiment.
Figure 5D:
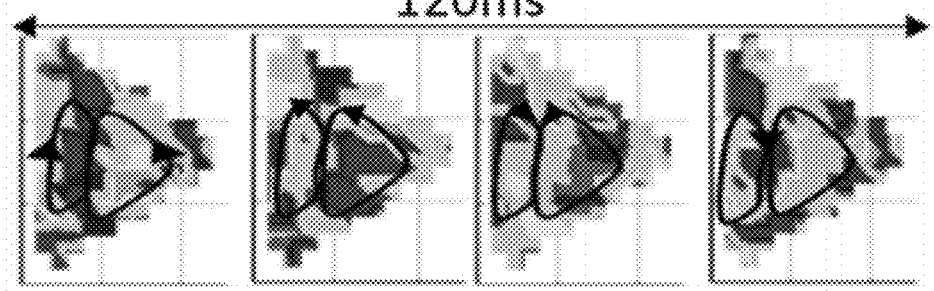
FIG. 5D shows repetitive figure-of-eight activation in the PLA in accordance with an illustrative embodiment.
Figure 5E:
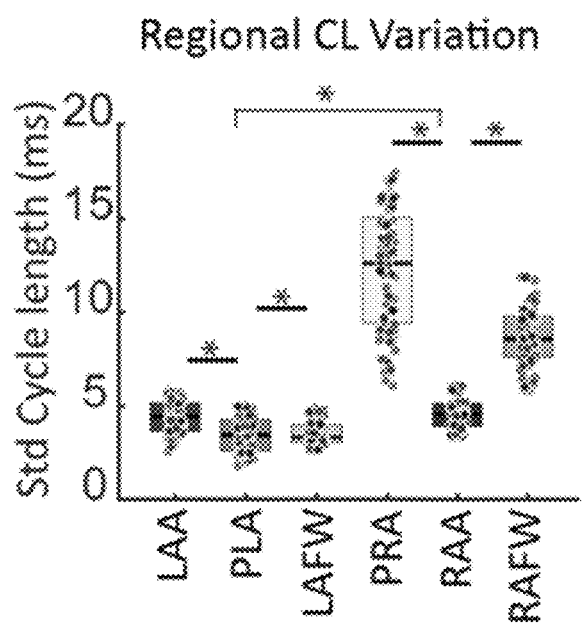
FIG. 5E shows regional cycle length variations (standard deviation of CL) with the highest CL variations in the right atrium in accordance with an illustrative embodiment.
Figure 5F:
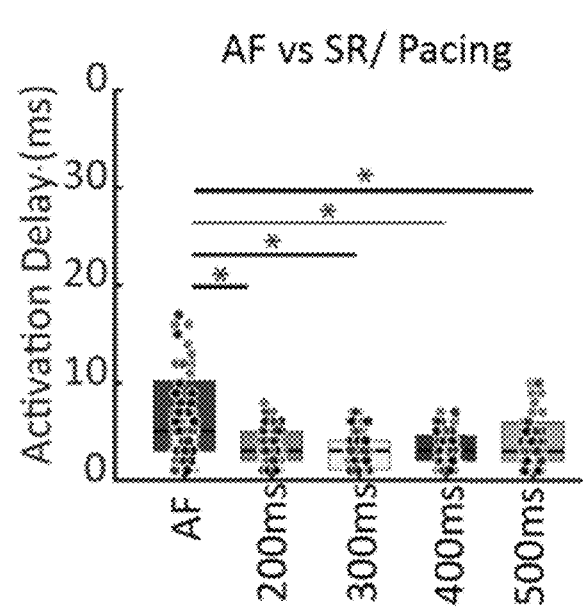
FIG. 5F depicts the decrease of activation delay (2x) when comparing AF with sinus rhythm/pacing intervals (200 ms to 500 ms) in accordance with an illustrative embodiment.

FIG. 5C shows bipolar signal recordings at reentry (CL of 90 ms) and more organized, nearly planar wave episode (CL of 120 ms) in the same region (RAA) and animal in accordance with an illustrative embodiment. Interestingly, figure-of-eight activations were also frequently observed at the same locations. FIG. 5D shows repetitive figure-of-eight activation in the PLA in accordance with an illustrative embodiment. Of note, the regional cycle length variation, shown as the standard deviation of CL, was higher in the right atrium (RA) compared to the left atrium (LA). The least variation suggest that these sites may be the most stable driver sites. FIG. 5E shows regional cycle length variations (standard deviation of CL) with the highest CL variations in the right atrium in accordance with an illustrative embodiment. It is therefore apparent that the conduction delay zones are a cycle length dependent phenomenon. Activation delay increased by a factor of 3-4 during AF compared to sinus rhythm or planar wave activation. Further, activation delay decreased significantly with increasing CL, when comparing AF and SR/paced rhythm with pacing intervals (200 ms to 500 ms). FIG. 5F depicts the decrease of activation delay (2×) when comparing AF with sinus rhythm/pacing intervals (200 ms to 500 ms) in accordance with an illustrative embodiment. FIG. 5F shows that the increase of slow conduction zone is an important relevant functional change and necessary condition which leads to AF/which is responsible for AF.

Activation patterns like focal source activity and activity around a line of block were reported in previous high-density AF mapping studies. Focal sources were described in nearly circular form with similar length and width size. In contrast, it was found that focal activities were often strongly asymmetric with significantly larger length, compared to the width. This activation pattern is defined as 'thin line activation'. Focal activities at the same locations between lines of block were frequently observed. The detected focal source dimensions and the number of focal sources per AF cycle were also determined. The detected lengths and widths of the focal activities were (4.9±5.0 mm, and 4.9±6.2 mm), range between 1-30 mm.

Figure 6A:
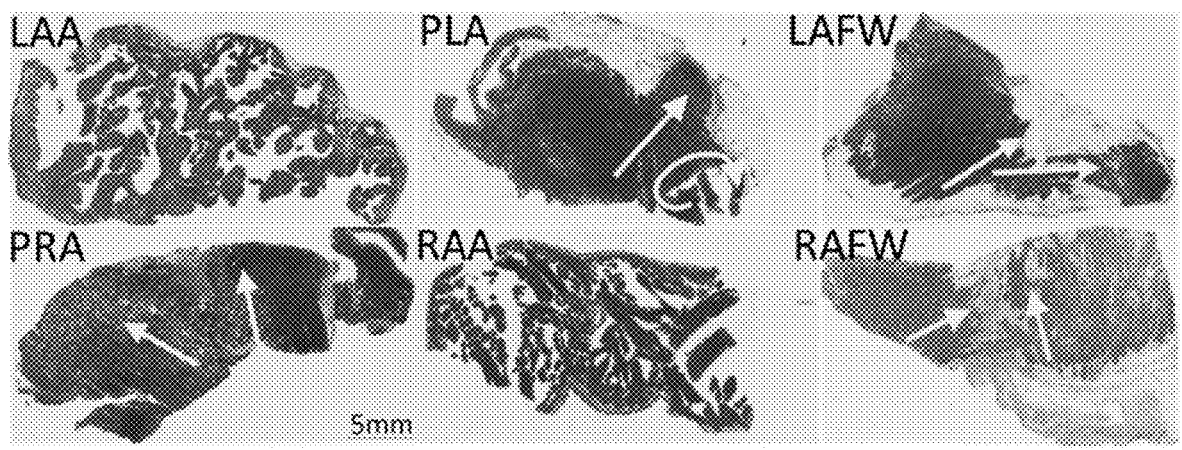
FIG. 6A shows the representative tissue sections in all six regions in animal #7 in accordance with an illustrative embodiment.
Figure 6B:
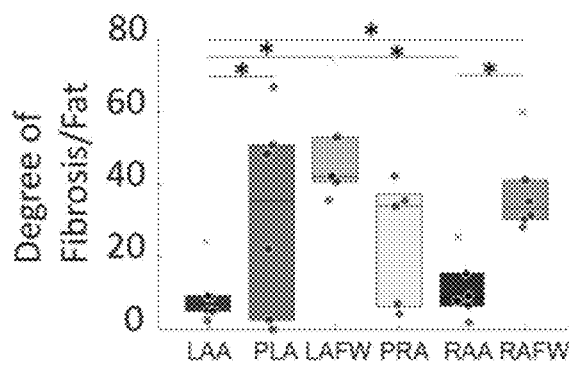
FIG. 6B depicts the degree of focal fibrosis in all bi-atrial regions in accordance with an illustrative embodiment.
Figure 6C:
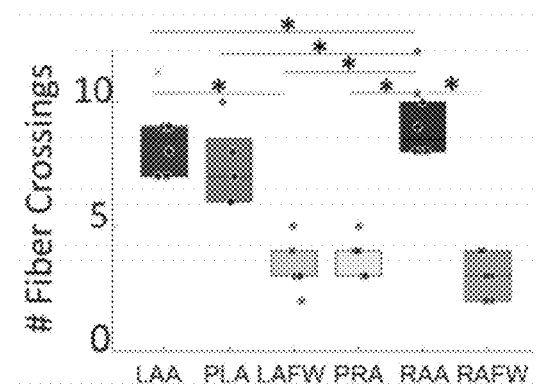
FIG. 6C depicts how the highest number of fiber crossings were detected in the RAA, LAA, and PLA (P-value significant) in accordance with an illustrative embodiment.
Figure 6D:
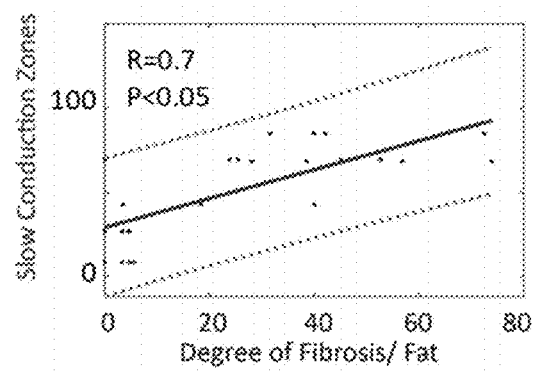
FIG. 6D shows correlation of the degree of fibrosis/fat with detected slow conduction zones (activation delay zones >10 ms) in accordance with an illustrative embodiment.

The inventors further analyzed the underlying substrate characteristics in all bi-atrial regions in six animals. FIG. 6A shows the representative tissue sections in all six regions in animal #7 in accordance with an illustrative embodiment. Dense focal fibrosis developed at fiber crossings (intersections of fiber lines). The highest degree of dense focal fibrosis/fat was detected in the LAFW (49±14%) and in the PLA (47±19%). FIG. 6B depicts the degree of focal fibrosis in all bi-atrial regions in accordance with an illustrative embodiment. There was no significant regional difference in macroscopic fiber anisotropy detected as the standard deviation of macroscopic fiber orientation. In contrast, the fiber crossings density, defined as the number of fiber crossings per tissue section, was significantly higher in the PLA, LAA, and in the right atrium in the RAA, compared to other atrial regions. FIG. 6C depicts how the highest number of fiber crossings were detected in the RAA, LAA, and PLA (P-value significant) in accordance with an illustrative embodiment. Importantly, the degree of focal fibro-fatty infiltration correlated closely with the detected number of slow conduction zones (R=0.8, P<0.01). FIG. 6D shows correlation of the degree of fibrosis/fat with detected slow conduction zones (activation delay zones >10 ms) in accordance with an illustrative embodiment. Slow conduction zones (>=2.5 mm×2.5 mm) located at fibrotic/fat tissue regions in histological tissue sections were studied as examples. These examples demonstrate low voltage (<1 mV) at these regions of slow conduction and anchored reentry.

Figure 6E:
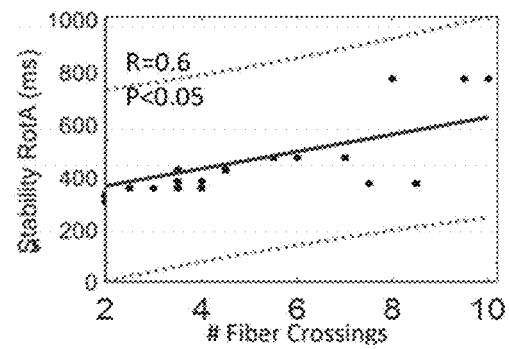
FIG. 6E shows correlation of macroscopic fiber crossings with the stability of rotational activity in accordance with an illustrative embodiment.
Figure 6F:
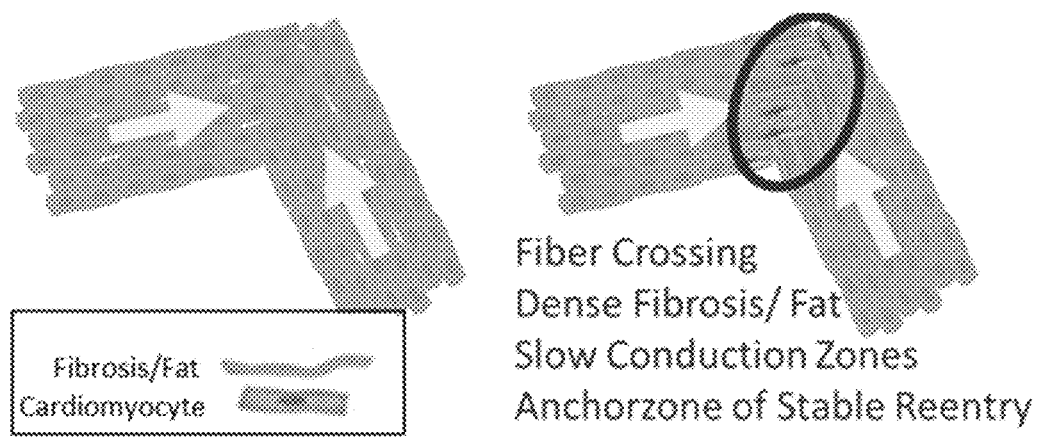
FIG. 6F shows a schematic of myocardial fiber crossing (left) and a schematic of a fiber crossing that develops to a dense fibrosis/fat zone (right) in accordance with an illustrative embodiment.

Furthermore, the stability of rotational activity correlated with the number of macroscopic fiber crossings per tissue section (R=0.6, P<0.05). FIG. 6E shows correlation of macroscopic fiber crossings with the stability of rotational activity in accordance with an illustrative embodiment. FIG. 6F shows a schematic of myocardial fiber crossing (left) and a schematic of a fiber crossing that develops to a dense fibrosis/fat zone (right) in accordance with an illustrative embodiment. This fiber crossing zone is also a slow conduction zone and anchor zone of rotational activity. Interestingly, nearly no dense fibrosis/fat zones were detected in the appendages, but about 1.5 fibrosis/fat regions per tissue section was detected in the other remaining bi-atrial regions. Importantly, more than 90% of the detected fibrosis and fat regions were located near macroscopic fiber crossings in the atrial regions. The sensitivity and specificity of dense fibro-fatty infiltrations at macroscopic fiber crossings were 98% and 58%. This data shows that slow conduction may be the product of increased fiber crossings as well as more fibrosis/fat.

The correlation between established EGM measures and rotational activities was also assessed. It was found that the stability of rotational activity correlated with the electrogram measures OI (R=0.68), FI (R=0.61), ShEn (R=0.58), and CL (R=0.56), but not with DF (R=0.28), (P<0.0001, for all comparisons except DF).

Figure 7A:
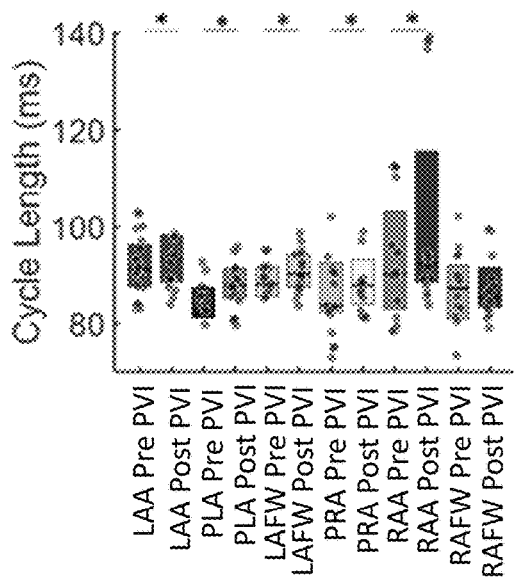
FIG. 7A shows how PVI led to a significant increase in CL in nearly all regions remote to the PVs in accordance with an illustrative embodiment.
Figure 7B:
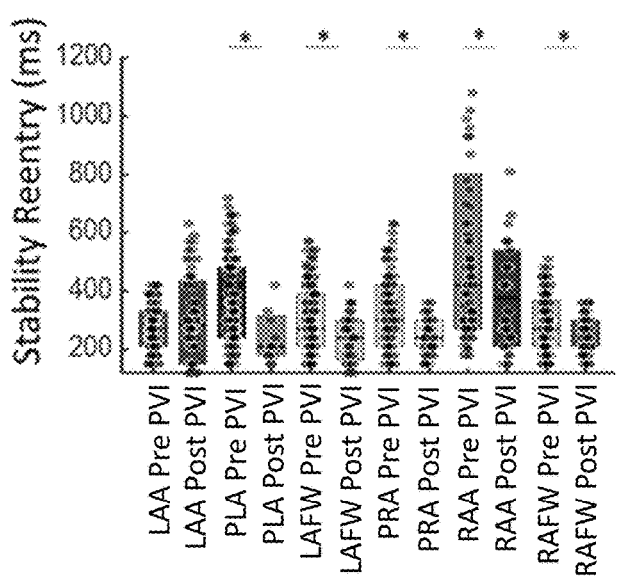
FIG. 7B depicts how the stability of rotational activity decreased significantly (baseline vs after PVI) in nearly all atrial regions in accordance with an illustrative embodiment.

The study also considered whether pulmonary vein isolation can reduce AF drivers remote to the pulmonary veins. Pulmonary vein isolation (PVI) is thought to be efficacious in patients with paroxysmal and persistent atrial fibrillation. However, the underlying mechanisms by which PVI leads to beneficial atrial remodeling are not clear. It was hypothesized that PVI, by eliminating the fastest rotational activity in the PLA and thereby leading to an increase in cycle length, affects rotational activity and slow conduction zones in atrial regions that are remote from the pulmonary veins. To assess the effects of PVI on rotational activity in the entire left and right atrium, epicardial PVI was performed in five dogs subjected to chronic rapid atrial pacing. The fastest rotational activity (with shortest CL) in these five animals was in the PLA. Importantly, PVI led to a significant increase in CL of rotational activity in the PLA, which was in turn accompanied by a decrease in the stability of rotational activity in this region. This decrease in the stability of rotational activities in the PLA was also accompanied by a decrease in the stability of rotational activities in nearly all atrial regions remote from the site of ablation. FIG. 7A shows how PVI led to a significant increase in CL in nearly all regions remote to the PVs in accordance with an illustrative embodiment. FIG. 7B depicts how the stability of rotational activity decreased significantly (baseline vs after PVI) in nearly all atrial regions in accordance with an illustrative embodiment.

Figure 7C:
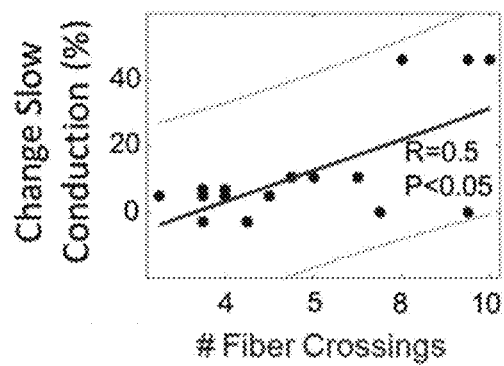
FIG. 7C shows the percentage reduction change of slow conduction zones pre vs post PVI correlated with the stability of rotational activity at baseline (R=0.5, P<0.05) in accordance with an illustrative embodiment.
Figure 7D:
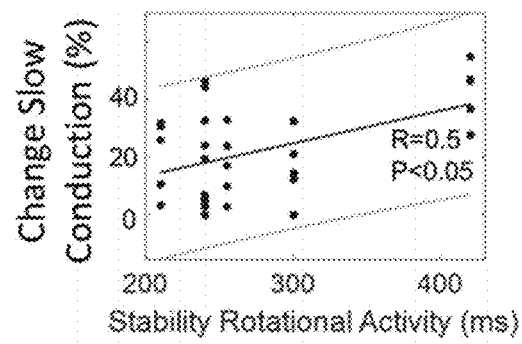
FIG. 7D depicts the number of fiber crossings per tissue section vs change of slow conduction after PVI (R=0.6, P<0.05) in accordance with an illustrative embodiment.

Despite this change in stability of rotational activities, slow conduction zones were similarly located in the same regions pre and post PVI, but reduced after PVI. Particularly, the percentage change in the number of slow conduction zones pre vs post-PVI was highest in the right atrial appendage (50% reduction in the number of slow conduction zones) and correlated with the number of macroscopic fiber crossing density in the histological tissue analysis. FIG. 7C shows the percentage reduction change of slow conduction zones pre vs post PVI correlated with the stability of rotational activity at baseline (R=0.5, P<0.05) in accordance with an illustrative embodiment. Furthermore, the change in the number of slow conduction zones post-PVI further correlated with the stability of rotational activity at baseline. FIG. 7D depicts the number of fiber crossings per tissue section vs change of slow conduction after PVI (R=0.6, P<0.05) in accordance with an illustrative embodiment. Taken together, these data show that PVI leads to a decrease in the stability of rotational activity in the PLA. CL-slowing resulting from the slowing of the fastest reentries in the PLA might also lead to a decrease in stability of rotational drivers throughout the atria by attenuating the conduction slowing at slow conduction zones in all these regions, and therefore reducing the anchoring of reentries.

The inventors also analyzed AF drivers and slow conduction in ten patients (age 66.0±7.3, male 60%) during early persistent AF undergoing ablation. Half of the patients had bi-atrial dilatation with a mean left atrium volume of 52.6±31.9 mL/m$^2$. The mean AF cycle length was 146±3 ms. Patient characteristics are summarized in the table of FIG. 2. Slow conduction at reentry sites and focal sources near the pulmonary veins were evaluated using the HD grid mapping catheter. Similar to the findings observed in the rapid atrial pacing model in animals, rotational activity trajectories had maximal activation delay zones at the edges of the reentrant circuits. FIG. 8A shows an activation time map of one AF cycle in the PLA that exhibits a reentrant circuit with a 2-6-fold higher activation delay at one edge of the reentrant trajectory compared to the other reentry trajectory segment parts in accordance with an illustrative embodiment. The study detected 2.3±1.6 (median 2) reentries and 2.1±1.1 (median 2) focal sources per AF cycle in the left atrium of these patients. FIG. 8B shows that activation delay and maximal activation delay at reentries per AF cycle were 9.3±8.8 ms (median 9.2 ms) and 20.2±8.1 ms (median 19.6 ms) along 2.5 in accordance with an illustrative embodiment. In addition, activation delay and maximal activation delay were 20.2±19.1 ms (median 15.7 ms) and 26.8±17.4 ms (median 24.4 ms) at focal sources per AF cycle. FIG. 8C shows three major zones of slow conduction on a representative left atrial bipolar voltage map and the corresponding activation time map in the Ensite NavX mapping system® (Abbott) in accordance with an illustrative embodiment. FIG. 8D shows how the activation delay was 2× higher in AF compared to SR/CS-pacing maps in accordance with an illustrative embodiment. This further illustrates that the cycle length dependence of the activation delay in slow conduction zones.

This study demonstrates that reentry and focal sources are frequently anchored between small slow conduction zones in all regions of the atria. In contrast to previous studies of persistent AF, the findings in this work are based on both open chest high-density mapping in a large animal model of AF and high-density endocardial mapping in humans using the HD-grid catheter. This study further demonstrates a critical role for slow conduction in the generation of rotational activities, with the conduction slowing being strongly dependent on cycle length. The study further demonstrates that AF drivers and slow conduction zones are highly correlated with macroscopic myofiber crossings and regions of fibro-fatty infiltration, based on the detailed histological analysis in all atrial regions.

This work provides a novel method for the automatic detection of reentries, their trajectories, and the detection of the additional small anchor zones in between reentries. In previous studies, the trajectory of reentries was calculated based on phase singularities. Unfortunately, a limitation of this method is that it can falsely detect phase singularities in the absence of rotors. In contrast, the new polygon method described herein can detect the entire rotor trajectory with much higher accuracy based on the earliest and latest activation and slow conduction.

Several previous studies showed that AF triggers outside the pulmonary veins (PVs) were located in the vena cavae, the crista terminalis, the coronary sinus, the ligament of Marshall, the inter-atrial septum, and the appendages. The central role of the PVs in the development and maintenance of AF has been demonstrated. Studies have also detected focal and rotor activity with spatial stability using low-resolution endocardial basket catheter and phase singularity AF mapping. Recently, a noninvasive mapping study in paroxysmal and persistent AF patients showed multiple (2-5) concurrent wavelets (92%), with both simultaneous focal activation from areas near the pulmonary veins (69%) and non-pulmonary veins (62%). However, reentry which sustained >1 rotation was rarely seen. In contrast, another noninvasive study showed AF drivers with 81% reentries and 20% focal breakthroughs with incessantly changing beat-to-beat wavefronts and spatiotemporal behavior. Another analysis performed a high-density sequential epicardial mapping study in patients with AF and showed epicardial breakthrough sites some intermittent focal activity (0.8%). Another study performed sequential, left and right atrial, epicardial mapping in patients with persistent AF and demonstrated intermittent foci (≤2 beats), and intermittent reentry (≥2 rotations), but neither sustained focal nor sustained reentrant activation was detected.

The findings of the present analysis are largely consistent with the previous reports, but the present work further characterized AF drivers with slow conduction regions in all bi-atrial regions. In this work, changing beat-to-beat wavefronts were observed, along with varying spatiotemporal behavior of driver activities. Reentrant activation as automatically detected with the novel algorithm was not sustained (median, 2.6 rotations lasting 449±89 ms), tended to meander, and recurred repetitively in the same region. Furthermore, the highest stability of the rotational activities was in the appendages and in PLA between small, frequency-dependent zones of slow conduction zones.

It was previously thought that reentry may be functional and not require an anatomically defined pathway. However, in this work, it was demonstrated that the reentrant circuit trajectories are more complex than circles or ovals like those previously historically described. Instead, the reentrant circuit trajectories follow line patterns with a curvature angle between lines, which appeared to be at least partially anchored to myofiber crossings or regions of fibro-fatty infiltrations.

Importantly, these findings are based on the developed method for AF driver detection with the earliest and latest activation result in a proposed new model of reentry. The proposed 'polygon' reentry model has the advantage that it describes both structural and functional characteristics of the reentry in contrast to the established reentry models in the last 100 years like the anatomic reentry around a fixed obstacle, or the functional models leading circle reentry model, and spiral wave model. FIG. 9A is a table comparing circus movement, leading circle, spiral wave, and the proposed polygon reentry models in accordance with an illustrative embodiment. In the circus movement reentry model, the anatomic reentry is around a fixed obstacle and allows for an excitable gap. In the leading circle reentry model, the conduction velocity (CV) and refractory period (RP) determine the circuit size. In addition, the center of the circuit is maintained refractory by centripetal wavelets. The spiral wave model describes a curved wavefront with a core of so-called phase singularity (PS), which rotates around an excitable but unexcited core. Previous models focused on the tip of the rotational activity analyzing the core with phase singularity points in phase maps. In contrast, the focus in the new model is the earliest and latest activation over time and slow conduction determined with activation delay within activation time maps. The proposed polygon reentry model describes both structural and functional characteristics with slow conduction zones at the edges of the propagation line patterns in form of a polygon.

Previous studies demonstrated that the main contributors to conduction and slow conduction in the heart are fiber orientation, ion channel characteristics, gap junction characteristics, and the presence of fibrosis/fat. It has also been demonstrated that conduction delay occurs at zones that reveal sudden changes in the fiber direction. These sites also have an abrupt increase in axial resistivity in the direction of propagation ensued, which may result in a decrease of the safety factor for propagation. It has further been demonstrated that zones of activation delay of up to 120 ms over distances as small as 3 mm in canine pulmonary veins correlated with abrupt changes in fascicle orientation. In the current study, slow conduction zones were found to not only be anchored to regions demonstrating myofiber crossings, fibrosis, or fat tissue zones, but were also found to be cycle length dependent. Furthermore, the number of macroscopic fiber crossings correlated closely with the stability of rotational activity. It was further discovered that regions of myofiber crossings had a much higher predilection to fibro-fatty infiltration than other myocardial regions. It is noted that almost no dense fibro-fatty zones were detected in the appendages.

FIG. 9B summarizes the main findings of the present study in accordance with an illustrative embodiment. Small conduction zones (>3 mm) may be at least partially myofiber crossings or regions of fibro-fatty infiltrations in all bi-atrial regions. At these fiber crossings zones, focal fibrosis and fat tissue developed. These fiber-crossing zones were frequency-dependent zones of activation delay and rotational activity frequently anchored between these small slow conduction zones. These zones were further located at the same locations in different rhythms or activation patterns (AF and sinus rhythm, rotational activity, and planar wave activation). Importantly, activation delay increased at these small conduction zones during rotational activity and decreased during planar wave activation or sinus rhythm. As discussed below, PVI increased CL and reduced the activation delay of these zones in all regions remote to the PVs. These activation delay zones at rotational activities were present in the animal model and patients. These findings result in the proposed polygon model for reentry. As described, slow conduction zones are located at abrupt changes in the fiber direction.

FIG. 9C depicts an example of the PLA in accordance with an illustrative embodiment. FIG. 9D depicts fiber orientation in the PLA with multiple fiber crossings near the pulmonary veins in accordance with an illustrative embodiment. Slow conduction zones at fiber crossings are marked with an asterisk. FIG. 9E is a schematic of the proposed polygon reentry model in accordance with an illustrative embodiment. The schematic shows both fibers and fibrosis at the edges of the reentry trajectory.

Another consideration is whether pulmonary vein isolation (PVI) can modify the arrhythmogenic substrate in the entire left and right atrium. PVI is thought to be efficacious in both patients with paroxysmal and persistent atrial fibrillation. Despite extensive research based on data which showed that pulmonary vein triggers can have an important effect on the initiation of AF and that PVI can significantly reduce AF, the underlying mechanisms by which PVI leads to beneficial atrial remodeling remain unclear. The findings described herein help explain, at least in part, why PVI leads to beneficial remodeling in both atria. PVI led to a significant slowing of rotational activities in the PLA. Since the stability of rotational activity was largely CL dependent, this increase in CL led to a significant decrease in the stability of rotational activity in the PLA. Since the rotational activity was fastest in the PLA at baseline with smallest variation in CL, slowing of rotational activity in this region also likely led to CL slowing in the rest of the left and right atrium. Interestingly, this CL increase was then associated with a significant decrease in stability of rotational activity in nearly all regions in the left and right atrium remote to the pulmonary veins. Despite this decrease in stability of rotational activity in all atrial sub-regions, residual rotational activity continued to be anchored to zones of slow conduction. These data suggest that in addition to performing PVI, it may be important to target remaining anchor zones of rotational and focal activities throughout the atria, including the appendages.

FIG. 10 is a diagram that shows use of the proposed techniques by a physician to identify and display reentry in accordance with an illustrative embodiment. As shown, a computing device is in communication with the sensors attached to the patient. Based on sensor data, the computing system determines various characteristics of the reentry and displays them for the physician to view. The displayed characteristics can include reentry locations in the heart, activation time maps that depict reentry, reentry stability, reentry cycle length, reentry slow CV, reentry trajectory, anchor points, various activation patterns, etc. The computing system can also calculate and display fastest/slowest CL, most stable reentry, reentry size, reentry frequency, slow conduction, reentry core, activation patterns, focal waves, planar waves, pre/post treatment data, etc. The proposed system provides reentry detection based on the parameters of earliest and latest activation. The system performs new reentry trajectory detection of driving earliest activation, and performs slow conduction detection at the edges of the trajectory. As shown in FIG. 10, the system also provides visual of clinically relevant reentry detections and characteristics.

Figure 11A:
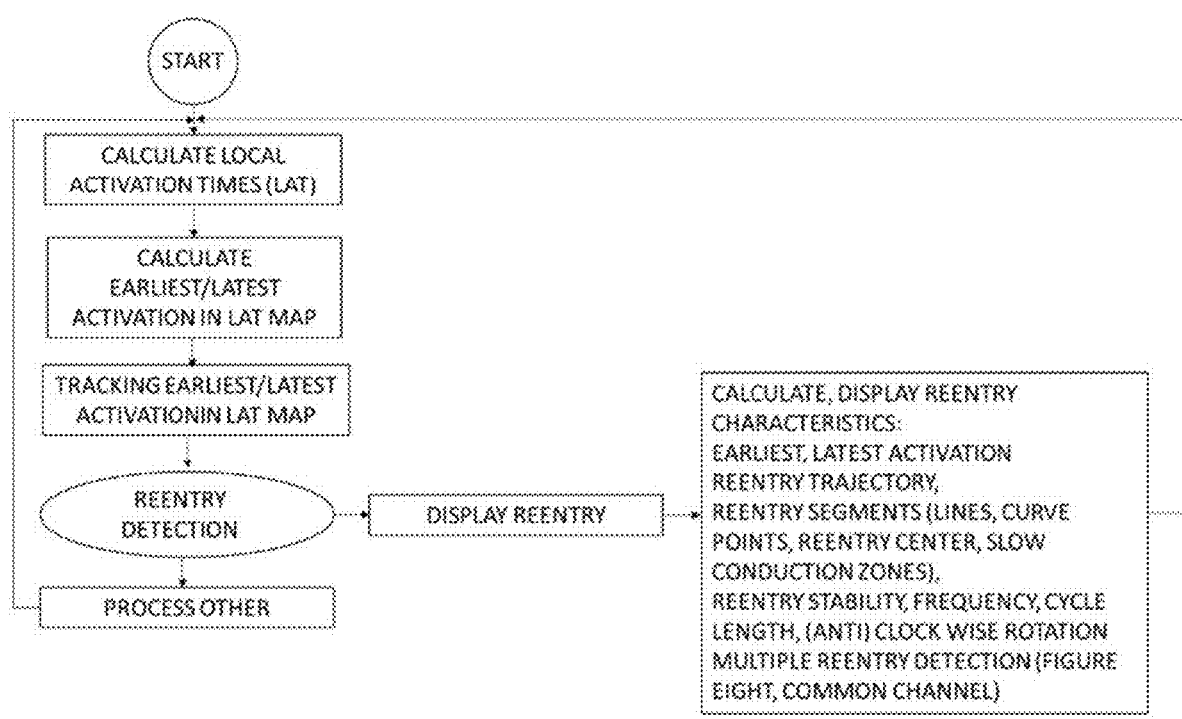
FIG. 11A is a flow diagram depicting operations performed by the system in accordance with a first illustrative embodiment.

FIG. 11A is a flow diagram depicting operations performed by the system in accordance with a first illustrative embodiment. In alternative embodiments, fewer, additional, and/or different operations may be performed. Also, the use of a flow diagram is not meant to be limiting with respect to the order of operations performed. Upon initiation by a user (e.g., a physician), the system calculates local activation times (LAT) based on data received from sensors mounted to a patient. Alternatively, the system may utilize previously obtained data that is stored in a memory. The system also calculates earliest and latest activation times based on the determined local activation times. The system generates a LAT map that displays the earliest and latest activation times. The system tracks (i.e., monitors the patient) the earliest and latest activation times in the LAT map. Upon reentry detection, the system determines and displays characteristics of the reentry. The characteristics can include earliest activation trajectory, latest activation trajectory, reentry segments (lines, curve points, reentry center, slow conduction zones, etc.), reentry stability, reentry frequency, cycle length, clockwise or counterclockwise rotation, multiple reentry detection (figure eight, common channel, etc.). The system can also perform any of the additional processing described herein upon detection of the reentry. The system then continues the cycle of monitoring, detection, and display. In another illustrative embodiment, the proposed algorithm for the detection of reentry trajectory based on the earliest and latest activation is programmed in Matlab. Alternatively, a different programming software may be used.

Figure 11B:
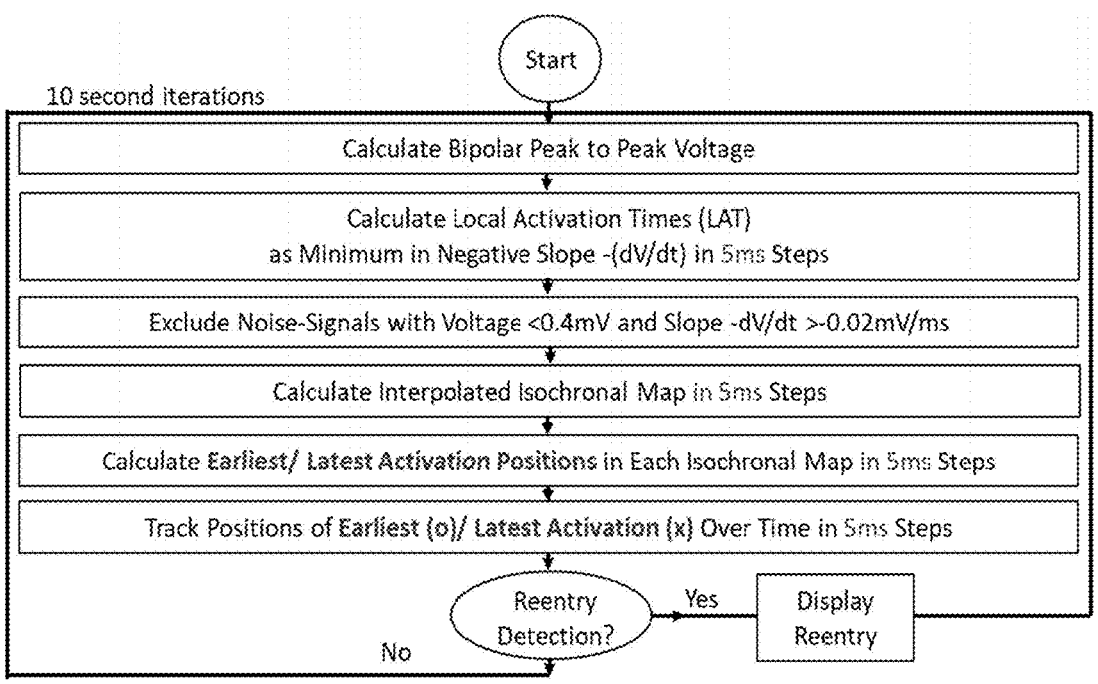
FIG. 11B is a flow diagram depicting operations performed by the system in accordance with a second illustrative embodiment.

FIG. 11B is a flow diagram depicting operations performed by the system in accordance with a second illustrative embodiment. As shown, in this embodiment, the bipolar peak-to-peak amplitude is calculated. Local activation time maps are also calculated as times of the minimum in the negative slope (dV/dt) in each 5 ms for 10 seconds. Signals with high noise-level are excluded with peak-to-peak voltage values <0.4 mV and steepest negative slope values >−0.02 mV/ms. In another operation, interpolated isochronal maps are calculated in 5 ms steps. Additionally, the positions of the earliest and latest activation are calculated in each isochronal map. In another operation, the algorithm tracks the earliest and latest activation over time in 5 ms steps. If a reentry loop is detected, the reentry is displayed. These iterative steps are calculated in 10-second windows. This algorithm also detects slow conduction zones and activation delay along the reentry trajectory of the earliest and latest activation. In alternative embodiments, different time values and/or voltage values may be used.

Figure 12:
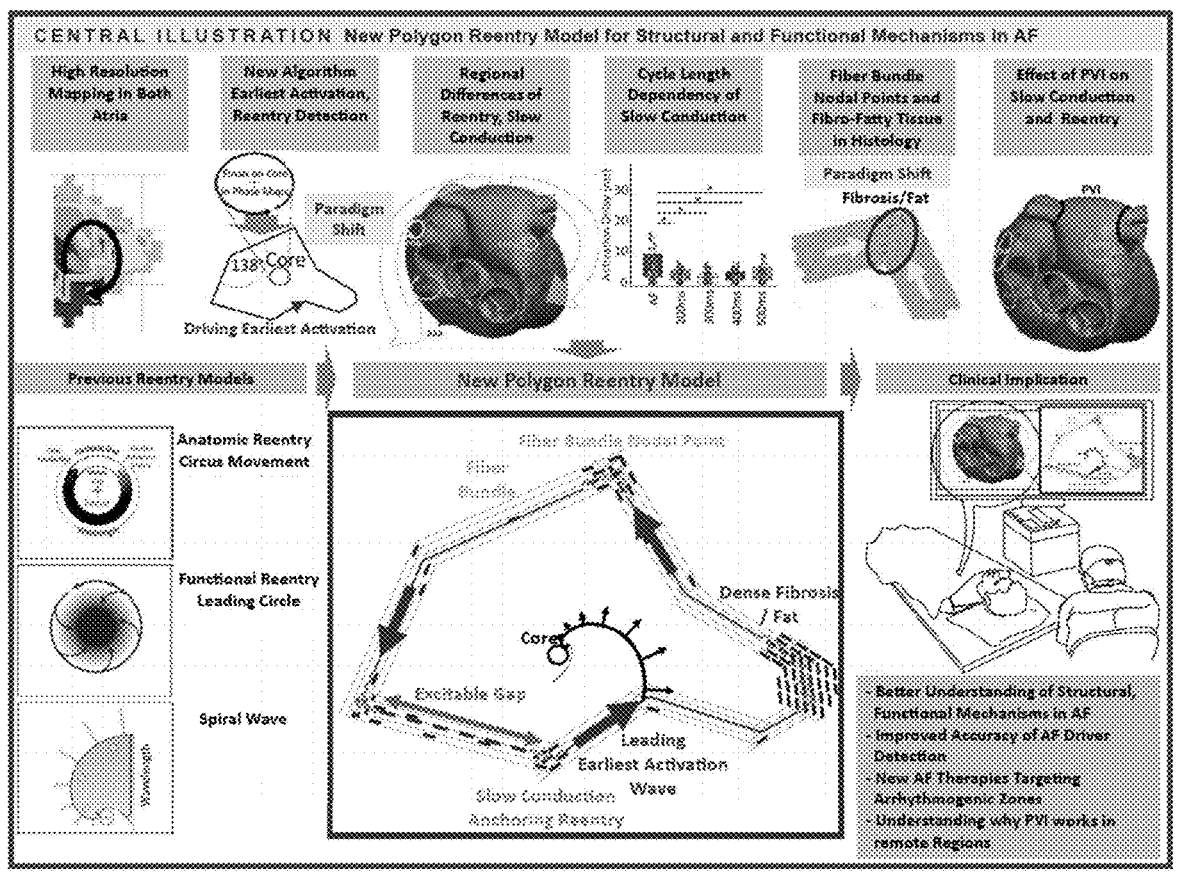
FIG. 12 is another flow diagram depicted a polygon reentry model for structural and functional mechanisms in atrial fibrillation in accordance with an illustrative embodiment.

FIG. 12 is another flow diagram depicted a polygon reentry model for structural and functional mechanisms in atrial fibrillation in accordance with an illustrative embodiment. In alternative embodiments, fewer, additional, and/or different operations may be performed. Also, the use of a flow diagram is not meant to be limiting with respect to the order of operations performed. The diagram depicts various operations performed by the polygon reentry model described herein. These operations include high resolution mapping in both atria, earliest activation reentry detection, identification of regional differences of reentry and slow conduction, determination of cycle length dependency of slow conduction, identification of fiber bundle nodal points and fibro-fatty tissue in histology, determination of the effect of PVI on slow conduction and reentry, etc. The diagram of FIG. 12 also depicts an example of dense fibrosis fat, a fiber bundle nodal point, a fiber bundle, an excitable gap, a slow conduction anchoring reentry, and a leading earliest activation wave. The diagram further describes various clinical implications of the polygon reentry model, including a better understanding of structural and functional mechanisms in AF, improved accuracy of AF driver detection, the ability to use new AF therapies targeting arrhythmogenic zones, developing an understanding of why PVI works in remote regions, etc.

In an illustrative embodiment, the proposed system can include and/or be in communication with a computing system that includes a memory, processor, user interface, transceiver, and any other computing components. Any of the operations described herein may be performed by the computing system. The operations can be stored as computer-readable instructions on a computer-readable medium such as the computer memory. Upon execution by the processor, the computer-readable instructions are executed as described herein. As an example, FIG. 13 is a block diagram of a system for performing analysis of AF data in accordance with an illustrative embodiment.

Figure 13:
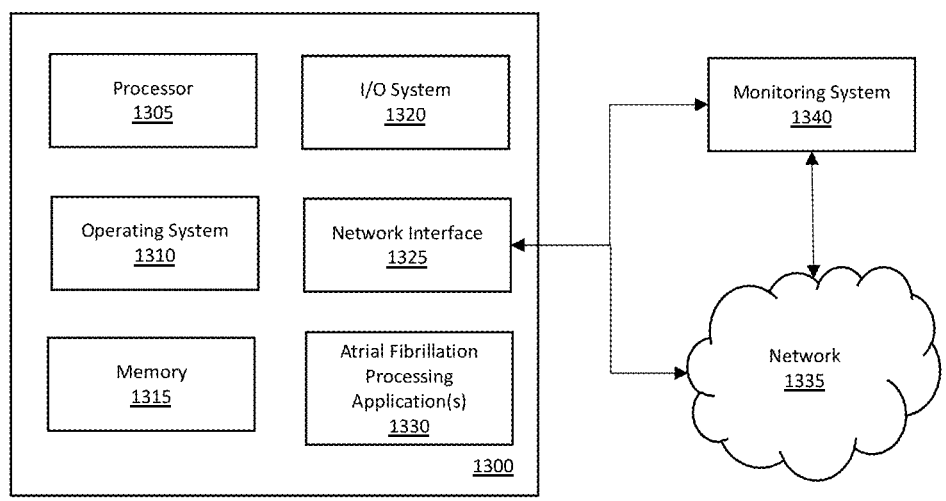
FIG. 13 is a block diagram of a system for performing analysis of AF data in accordance with an illustrative embodiment.

FIG. 13 depicts a computing device 1300 in communication with a network 1335 and a monitoring system 1340. The monitoring system 1340 can be an HD grid catheter and electrodes as described herein. The monitoring system 1340 can also include an imaging system such as an MRI system, or any other type of imaging system that is known in the art. The computing device 1300 includes a processor 1305, an operating system 1310, a memory 1315, an input/output (I/O) system 1320, a network interface 1325, and AF processing application(s) 1330. In alternative embodiments, the computing device 1300 may include fewer, additional, and/or different components. The components of the computing device 1300 communicate with one another via one or more buses or any other interconnect system. The computing device 1300 can be any type of networked computing device such as a laptop computer, desktop computer, smart phone, tablet, workstation, server, etc.

The processor 1305 can be in electrical communication with and used to control any of the system components described herein. The processor 1305 can be any type of computer processor known in the art, and can include a plurality of processors and/or a plurality of processing cores. The processor 1305 can include a controller, a microcontroller, an audio processor, a graphics processing unit, a hardware accelerator, a digital signal processor, etc. Additionally, the processor 1305 may be implemented as a complex instruction set computer processor, a reduced instruction set computer processor, an x86 instruction set computer processor, etc. The processor 1305 is used to run the operating system 1310, which can be any type of operating system.

The operating system 1310 is stored in the memory 1315, which is also used to store programs, user data, network and communications data, peripheral component data, the AF processing application(s) 1330, and other operating instructions. The memory 1315 can be one or more memory systems that include various types of computer memory such as flash memory, random access memory (RAM), dynamic (RAM), static (RAM), a universal serial bus (USB) drive, an optical disk drive, a tape drive, an internal storage device, a non-volatile storage device, a hard disk drive (HDD), a volatile storage device, etc.

The I/O system 1320 is the framework which enables users and peripheral devices to interact with the computing device 1300. The I/O system 1320 can include a mouse, a keyboard, one or more displays (e.g., light-emitting diode display, liquid crystal display, touch screen display, etc.), a speaker, a microphone, etc. that allow the user to interact with and control the computing device 1300. The I/O system 1320 also includes circuitry and a bus structure to interface with peripheral computing devices such as power sources, the monitoring system 1340, USB devices, data acquisition cards, peripheral component interconnect express (PCIe) devices, serial advanced technology attachment (SATA) devices, high definition multimedia interface (HDMI) devices, proprietary connection devices, etc.

The network interface 1325 includes transceiver circuitry that allows the computing device to transmit and receive data to/from other devices such as the monitoring system 1340, remote computing systems, servers, websites, etc. The network interface 1325 enables communication through the network 1335, which can be one or more communication networks. The network 1335 can include a cable network, a fiber network, a cellular network, a wi-fi network, a landline telephone network, a microwave network, a satellite network, etc. The network interface 1325 also includes circuitry to allow device-to-device communication such as Bluetooth® communication.

The AF processing application(s) 1330 can include software and algorithms in the form of computer-readable instructions which, upon execution by the processor 1305, performs any of the various operations described herein such as processing data received from the monitoring system 1340, calculating bipolar peak-to-peak voltages, calculating local activation times, excluding noise signals from the activation times, calculating interpolated isochronal maps, calculating earliest/latest activation positions in each isochronal map, tracking positions of earliest/latest activation over time, determining whether reentry is detected, performing other analyses, generating plots, analyzing the plots, solving equations, identifying reentry trends, etc. The AF processing application(s) 1330 can utilize the processor 1305 and/or the memory 1315 as discussed above. In an alternative implementation, the AF processing application(s) 1330 can be remote or independent from the computing device 1300, but in communication therewith.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A method for characterizing atrial fibrillation comprising:
    determining, by a processor of a computing device and based on heart data, an earliest activation time of a heart being monitored;
    determining, by the processor and based on the heart data, a latest activation time of the heart;
    modeling, by the processor, the earliest activation time and the latest activation time within one or more activation time maps;
    identifying, by the processor, one or more rotational activity trajectories based on the one or more activation time maps;
    identifying a plurality of propagation line patterns based on the one or more rotational activity trajectories;
    forming a polygon from the plurality of propagation line patterns; and
    identifying, by the processor, an atrial fibrillation driver based at least in part on the polygon.

2. The method of claim 1, further comprising receiving, by a network interface of the computing device, the heart data from a monitoring system that includes a grid catheter and a plurality of electrodes.

3. The method of claim 1, further comprising determining, by the processor and based on the heart data, an activation delay of the heart.

4. The method of claim 3, wherein the atrial fibrillation driver is based at least in part on the activation delay.

5. The method of claim 1, further comprising identifying, by the processor, one or more slow conduction regions of the heart based at least in part on the one or more activation time maps.

6. The method of claim 5, further comprising identifying a location of a fiber crossing, a fibrosis, or a fat region, wherein the one or more slow conduction regions are identified based at least in part on the location of the fiber crossing, the fibrosis, or the fat region.

7. The method of claim 1, further comprising identifying one or more focal source locations based on the one or more rotational activity trajectories.

8. The method of claim 1, further comprising performing a pulmonary vein isolation (PVI) on the heart.

9. The method of claim 1, further comprising determining, by the processor, a reentry trajectory and displaying the reentry trajectory on a display.

10. The method of claim 1, wherein the plurality of propagation line patterns form edges of the polygon, and wherein the atrial fibrillation driver is identified at one or more of the edges of the polygon.

11. A system to characterize atrial fibrillation, the system comprising:
    a memory configured to store heart data;
    a processor operatively coupled to the memory and configured to:
    determine, based on heart data, an earliest activation time of a heart associated with the heart data;
    determine, based on the heart data, a latest activation time of the heart;
    model the earliest activation time and the latest activation time within one or more activation time maps; and
    identify one or more rotational activity trajectories based on the one or more activation time maps;
    identify a plurality of propagation line patterns based on the one or more rotational activity trajectories;
    form a polygon from the plurality of propagation line patterns; and
    identify an atrial fibrillation driver based at least in part on the polygon.

12. The system of claim 11, wherein the processor is further configured to determine, based on the heart data, an activation delay of the heart.

13. The system of claim 12, wherein the atrial fibrillation driver is based at least in part on the activation delay.

14. The system of claim 11, wherein the processor is further configured to identify one or more slow conduction regions of the heart based at least in part on the one or more activation time maps.

15. The system of claim 14, wherein the processor is further configured to identify a location of a fiber crossing, a fibrosis, or a fat region, wherein the one or more slow conduction regions are identified based at least in part on the location of the fiber crossing, the fibrosis, or the fat region.

16. The system of claim 11, wherein the processor is configured to identify one or more focal source locations based on the one or more rotational activity trajectories.

17. The system of claim 11, wherein the processor is further configured to perform a pulmonary vein isolation (PVI) on the heart.

18. The system of claim 11, wherein the plurality of propagation line patterns form edges of the polygon, and wherein the atrial fibrillation driver is identified at one or more of the edges of the polygon.

* * * * *